US006303846B1

(12) United States Patent
Scelonge et al.

(10) Patent No.: US 6,303,846 B1
(45) Date of Patent: Oct. 16, 2001

(54) **GENE ENCODING OXALATE DECARBOXYLASE FROM *ASPERGILLUS PHOENICES***

(75) Inventors: Christopher J. Scelonge, Des Moines; Dennis L. Bidney, Urbandale, both of IA (US)

(73) Assignee: Pioneer Hi-Bred International, Inc., Des Moines, CA (US)

(*) Notice: Subject to any disclaimer, the term of this patent is extended or adjusted under 35 U.S.C. 154(b) by 0 days.

(21) Appl. No.: 09/290,202

(22) Filed: Apr. 12, 1999

Related U.S. Application Data

(62) Division of application No. 08/821,827, filed on Mar. 21, 1997.

(51) Int. Cl.$^7$ .............................. C12N 5/04; C12N 15/31; C12N 15/55; C12N 15/82; A01H 5/00

(52) U.S. Cl. ..................... 800/279; 800/288; 800/301; 800/306; 800/322; 800/312; 800/313; 435/468; 435/419; 435/418; 435/416; 435/415

(58) Field of Search ......................... 800/279, 301, 800/322, 312, 313, 306, 288; 435/418, 419, 426, 428, 415, 416, 468

(56) References Cited

U.S. PATENT DOCUMENTS

| 5,488,035 | 1/1996 | Rao . |
| 5,547,870 | 8/1996 | Datta et al. . |

FOREIGN PATENT DOCUMENTS

| WO 92/14824 | 9/1992 | (WO) . |
| WO 94/12622 | 6/1994 | (WO) . |
| WO 94/13790 | 6/1994 | (WO) . |
| WO 96/30530 | 10/1996 | (WO) . |

OTHER PUBLICATIONS

Neuhaus, J. et al., "High–level expression of a tobacco chitinase gene in *Nicotiana sylvestris*. Susceptibility of transgenic plants to Cercospora nicotianae infection." 1991, Plant Mol. Biology, vol. 16, pp. 141–151.*
An, et al.—Jan. 1989, *Plant Cell,* 1:115–122, "Functional Analysis of the 3' Control Region of the Potato Wound–Inducible Proteinase Inhibitor II Gene".
Atanassvoa, et al.—1992, *Plant Journal,* 2(3):291–300, "A 126 bp fragment of a plant histone gene promoter confers preferenctial expression in meristems of transgenic Arabidopsis".
Ausubel, et al., (eds.)—1989, *Current Protocols in Molecular Biology,* John Wiley and Sons, Inc., pp. 1.03–1.15.8 and 2.0.1–2.12.5.
Beck, et al.—Oct. 1982, *Gene,* 19:327–336, "Nucleotide sequence and exact localization of the neomycin phosphotransferase gene from transposon Tn5".
Bevan, et al.—Nov.2, 1983, *Nucl. Acids Res.,* 11(2):369–385, "Structure and transcription of the nopaline synthase gene region of T–DNA".
Bevan, et al.—Nov. 22, 1984, *Nucl. Acids Res.,* 12:8711–8721, "Binary Agrobacterium vectors for plant transformation".
Bidney, et al.—1992, *Plant Mol. Biol.* 18:301–313, "Microprojectile bombardment of plant tissues increases transformation frequency by *Agrobacterium tumefaciens*".
Burrus, et al.—1991, *Plant Cell Rep,* 10:161–166, "Regeneration of fertile plants from protoplasts of sunflower (*Helianthus annus* L.)".
Christensen, et al.—1989, *Plant Mol. Biol,* 12:619–632, "Sequence analysis and transcriptional regulation by heat shock of polyubiquitin transcripts from maize".
Christensen, et al.—1992, *Plant Mol. Biol.,* 18:675–689, "Maize polyubiquitin genes: structure, thermal perturbation of expression and transcript splicing, and promoter activity following transfer to protoplasts by electroporation".
Christou, et al.—Jun. 1987, *PNAS USA,* 84:3962–3966, "Stable transformation of soybean by electroporation and root formation from transformed callus".
Cornish–Bowden, A.—May 10, 1985, *Nucleic Acids Res.,* 13:3021–3030, "Nomenclature for incompletely specified bases in nucleic acid sequences: recommendations 1984".
D'Halluin, et al.—Dec. 1992, *Plant Cell,* 4:1495–1505, "Transgenic Maize Plants by Tissue Electroporation".
DeLoose, et al.—Mar. 1, 1991, *Gene,* 99:95–100, "The extensin signal peptide allows secretion of a heterologous protein from protoplasts".
Deshayes, et al.—1985, *EMBO J.,* 4:2731–2737, "Liposome–mediated transformation of tobacco mesophyII protoplasts by an *Escherichia coli* plasmid".
Draper, et al.—1982, *Plant & Cell Physiol.,* 23(3):451–458, "Ti Plasmid Homologous Sequences Present in Tissues from Agrobacterium Plasmid–transformed Petunia Protoplasts".
Dratewka–Kos, et al., Mar. 25, 1989, *J. Biol. Chem.,* 264:4896–4900, "Polypeptide Structure of Germin as Deduced from cDNA Sequencing".
Dumas, et al.—1994, Abstracts: *4$^{th}$Int'l Congress of Plant Molecular Biology, #1906,* "Transgenic crops expressing oxalate oxidase as a way to increase tolerance to oxalate–producing fungi".
Emiliani, et al.—1964, *ARCH. Biochem. Biophys.,* 105:488:493, "Enzymatic Oxalate Decarboxylation in *Aspergillus niger*".
Enjuto, et al., May 1995, *Plant Cell,* 7:517–527, "Expression of the Arabidopsis HBG2 Gene, Encoding 3–Hydroxy–3–Methylglutaryl Coenzyme A. Reductase, is Restricted to Meristematic and Floral Tissues".

(List continued on next page.)

Primary Examiner—David T. Fox
Assistant Examiner—Anne Kubelik
(74) Attorney, Agent, or Firm—Pioneer Hi-Bred International, Inc.

(57) ABSTRACT

A novel nucleic acid sequence encoding *Aspergillus phoenices* oxalate decarboxylase (APOXD) has been determined, as well as the encoded amino acid sequence. The gene and its encoded protein are useful in degrading oxalate, in diagnostic assays of oxalate, and as a selectable marker.

5 Claims, 5 Drawing Sheets

OTHER PUBLICATIONS

Gatz, et al.—Jun. 1991, *Mol. Gen. Genetics,* 243:32–38, "Regulation of a modified CaMV 35S promoter by the Tn–10–encoded Tet repressor in transgenic tobacco".

Gruber, et al.—1993, Glick and Thompson, eds., CRC Press, inc., Boca Raton, pp. 89–119, "Vectors for Plant Transformation" In: *Methods in Plant Molecular Biology and Biotechnology.*

Guerrero, et al.—Mar. 9, 1990, *Mol. Gen. Genet.,* 224:161–168, "Promoter sequences from a amaize pollen–specific gene direct tissue–specific transcription in tobacco".

Hain, et al.—1985, *Mol. Gen. Genet.,* 199:161–168, "Uptake, integration, expression and genetic transmission of a selectable chimaeric gene by plant protoplasts".

Heney and Orr—May 1, 1981, *Anal. Biochem.,* 114:92–96, "The Purification of Avidin and Its Derivatives on 2–Iminobiotin–6–aminohexyl–Sepharose 4B".

Hershey, et al.—Oct. 1991—*Plant Mol. Biol.,* 17:679–690, "Isolation and characterization of cDNA clones for RNA species induced by substituted benzenesulfonamides in corn".

Hiei, et al.—Apr. 25, 1994, *The Plant Journal,* 6(2):271–282, "Efficient transformation of rice (*Oryza sativa*L.) medicated by Agrobacterium and sequence analysis of the boundaries of the T–DNA".

Holsters, et al.—1978, *Mol. Gen. Genetics,* 163–181–7, "Transfection and Transformation of *Agrobacterium tumefaciens*".

Horsch, et al.—Mar. 8, 1985, *Science,* 227:1229–31, "A Simple and General Method for Transferring Genes into Plants".

Johnson, et al.—1964, *Biochem. Biophys. Acta,* 89:351–353, "Use of a purified bacterial formate dehydrogenase for the micro–estimation of formate".

Kado—1991, *Crit. Rev. Plant Sci.,* 10(1):1–32, "Molecular Mechanism of Crown Gall Tumorigenesis".

Keil, et al.—Nov. 14, 1986, *Nucl. Acids Res.,* 14:5641–5650, "Primary Structure of a proteinase inhibitor II gene from potato (*Solanum tubercrosum*)".

Klein, et al.—Mar. 1992, *Biotechnology,* 10:286–291, "Transformation of Microbes, Plants and Animals by Particle Bombardment".

Kozak—Nov. 1989, *Mol. and Cell Biol.,* 9:5073–5080, "Context Effects and Inefficient Initiation at Non–AUG Codons in Eucaryotic Cell–Free Translation Systems".

Laker, et al.—Jan. 3, 1980, *Clin. Chem.,* 26(7):827–830, "Spectrophotometric Determination of Urinary Oxalate with Oxalate Oxidase Prepared from Moss".

Lane, et al.—Jun. 5, 1991, *J. Biol. Chem.,,* 266:10461, "Homologies between Members of the Germin Gene Family in Hexaploid Wheat and Similarities between These Wheat Germins and Certain Physarum Spherulins".

Last, et al.—1991, *Theor. Appl. Genet.,* 81:581–588, "pEmu: an improved promoter for gene expression in cereal cells".

Lathika, et al.—1995, *Anal. Lett.,* 28:425–442, "Determination of Urinary Oxalate Using Banana Oxalate Oxidase: Comparison with Immobilized Enzyme".

Laursen, et al.—Sep. 1994, *Plant Molecular Biology,* 24:51–61, "Production of fertile transgenic maize by electroporation of suspension culture cells".

Lepetit, et al.—1992, *Mol. Gen. Genet.,* 231:276–285, "A plant histone gene promoter can direct both replication–dependent and–independent gene expression in transgenic plants".

Lund, et al.—1992, *Plant Mol. Biol.,* 18:47–53, "A plant signal sequence enhances the secretion of bacterial ChiA in transgenic tobacco".

Lung, et al.—Apr. 1994, *J. Bacteriology,* 176:2468–2472, "Molecular Cloning, DNA Sequence, and Gene Expression of the Oxalyl–Coenzyme A Decarboxylase Gene, oxc, from the Bacterium *Oxalobacter formigenes*".

Malone–Schonberg, et al.—Sep. 1994, *Plant Science,* 103:199–207, "Stable transformation of sunflower using Agrobacterium and split embryonic axis explants".

Martin, et al.—Apr. 1993, *The Plant Journal,* 4:367–377, "Expression of an Arabidopsis sucrose synthase gene indicates a role in metabolization of sucrose both during phloem loading and in sink organs".

Martini, et al.—1993, *Mol. Gen. Genet.,* 236:179–186, "Promoter sequences of a potato pathogenesis–related gene mediate transcriptional activation selectively upon fungal infection".

Matsuoka, et al.—Feb. 1991, *PNAS USA,* 88:834–838, Propeptide of a precursor to a plant vacuolar protein.

McElroy, et al.—Feb. 1990, *Plant Cell,* 2:163–171, "Isolation of an Efficient Actin Promoter for Use in Rice Transformation".

Mehta and Datta—Dec. 15, 1991, *The Journal of Biological Chemistry,* 266(35):23548–23552, 1991, "Oxalate Decarboxylase from *Collybia velutipes*".

Mett, et al.—May 1993, *PNSA USA,* 90:4567–4571, "Copper–controllable gene expression system for whole plants".

Miki, et al.—1992, Glick and Thompson, eds., CRC Press, Inc., Boca Raton, pp. 67–88, "Procedures for Introducing Foreign DNA into Plants", In: *Methods in Plant Molecular Biology and Biotechnology.*

Mogen, et al.—Dec. 1990, *Plant Cell,* 2:1261–1272, "Upstream Sequences Other than AAUAAA Are Required for Efficient Messenger RNA 3'–End Formation in Plants".

Moloney, et al.—1989, *Plant Cell Reports,* 8:238–242, "High efficiency transformation fo *Brassica napus* using Agrobacterium vectors".

Mouly, et al.—Apr. 1992, *Plant Science,* 85:51–59, "Differential accumulation of hydroxyproline–rich glycoprotein transcripts in sunflower plants infected with *Sclerotinia sclerotiorum* or treated with oxalic acid".

Murai, et al.—1983, *Science,* 222:476–482, "Phaseolin Gene from Bean Is Expressed After Transfer to Sunflower Via tumor–Incuding Plasmid Vectors".

Obzansky, et al.—Jul. 1983, *Clinical Chem.,* 29(10):1815–1819, "Quantification of Urinary Oxalate with Oxalate Oxidase from Beet Stems".

Odell, et al.—Feb. 1985, *Nature,* 313:810–812, "Identification of DNA sequences required for activity of the cauliflower mosaic virun 35S promoter".

Roder, et al.—1994, *Mol. Gen. Genet.,* 243:32–38, "Efficiency of the tetracycline–dependent gene expression system: complete suppression and efficient induction of the rolB phenotype in transgenic plants".

Rychlik, et al.—Oct. 6, 1989, *Nucleic Acids Research,* 17(21):8543–8551, "A computer program for choosing optimal oligonucleotides for filter hybridization, sequencing and in vitro amplication of DNA".

Sanford—Dec., 1988, *Trends Biotech,* 6:299–302, "The biolistic process".

Sanford—1990, *Physiol. Plant,* 79:206–209, "Biolistic plant transformation".

Sanford, et al.—1987, *Part. Sci. and Technol.,* 5:27–37, "Delivery of Substances into Cells and Tissues Using a Particle Bombardment Process".

Schena, et al.—Dec. 1991, *PNSA U.S.A.,* 88:10421–10425, "A steroid–inducible gene expression system for plant cells".

Sengupta–Gopalan, et al.—May 1985, *PNAS USA,* 82:3320–3324, "Developmentally regulated expression of the bean β–phaseolin gene in tobacco seed".

Simpson, et al.—1985, *EMBO J.,* 4(11):2723–2729, "Light–inducible and tissue–specific expression of a chimaeric gene under control of the 5'–flanking sequence of a pea chlorophyII a/b–binding protein gene".

Innis, et al., (eds)—1990, In: *PCR Protocols,* "A guide to Methods and Applications", Academic Press, San Diego, CA, pp. 28–45 and 282–287.

Thompson, et al.—1995, *Euphytica,* 85:169–172, "Degradation of oxalic acid by transgenic oilseed rape plants expressing oxalate oxidase".

Timko, et al.—Dec. 12, 1985, *Nature,* 318:579–582, "Light regulation of plant gene expression by an upstream enhancer–like element".

Triebig and Schaller—1980, *Clin. Chem. Acta,* 108:355–360, "A Simple and Reliable Enzymatic Assay for the Determinatino of Formic Acid Urine".

Tsukaya, et al.—1993, *Mol. Gen Genet.,* 237:26–32, "Floral organ–specific and constitutive expression of an *Arabidopsis thaliana* heat–shock HSP18.2::GUS fusion gene is retained even after homeotic conversion of flowers by mutation".

Twell, et al.—1989, *Mol. Gen. Genet.,* 217:240–245, "Isolation and expression of an anther–specific gene from tomato".

Twell, et al.—1993, *Sex. Plant Reprod.,* 6:217–224, "Activation and developmental regulation of an Arabidopsis anther–specific promoter in microspores and pollen of *Nicotiana tabacum*".

Velten, et al., 1984, *EMBO J.,* 3(12):2723–2730, "Isolation of a dual plant promoter fragment from the Ti plasmid of *Agrobacterium tumefaciens*".

Verwoert, et al.—1994, *Plant Mol. Biol.,* 26:189–202, "Developmental specific expression and organelle targeting of the *Escherichia coli* fabD gene, encoding malonyl coenzyme A–cyl carrier protein transacylase in transgenic rape and tobacco seeds".

Ward, et al.—1993, *Plant Molecular Biol.,* 22:361–366, "Chemical regulation of trangene expression in plants".

Wilkins, et al.—Apr. 1990, *Plant Cell,* 2:301–313, "Role of Propeptide Blycan in Post–Translational Processing and Transport of Barley Lectin to Vacuoles in Transgenic Tobacco".

Zhang, et al.—1991, *Bio/Technology,* 9:996, "Efficient Transformation of Tobacco by Ultrasonication".

Gendler S.M., et al. (1981). Clinical Chemistry., vol. 27, No. 6, 1032, "2 Enzymes with potential use in spectrophotometric oxalate determination".

Napoli, et al.—Apr. 1990, *The Plant Cell.,* vol. 2, 279–289, "Introduction of a Chimeric Chalcone Synthase Gne into Petunia Results in Reversible Co–Suppression of Homologous Genes in trans".

Institute of Plant Sciences—1991, *Annu. Rev. Plant Physiol Plant Mol. Biol.,* 42:205–225, "Gene Transfer to Plants: Assessment of Published Approaches and Results".

Bidney, et al.—1992, *Plant Molecular Biology,* 18:310–313, "Microprojectile bombardment of plant tissues increases transformation frequency by *Agrobacterium tumefaciens*".

Carvalho, et al.—1992, *The EMBO Journal,* vol. 11, No. 7, 2595–2602, "Suppression of β–1, 3–glucanase transgene expression in homozygous plants".

Finnegan and McElroy—Sep. 1994, *Bio/Technology,* vol. 12, 83–888, "Transgene Inactivation: Plants Fight Back!".

Matzke and Matzke—1995, *Plant Physiol.,* 107: 679–685, "How and Why Do Plants Inactivate Homologous (Trans) genes?".

Barrett, et al.—1997, *Plant Cell, Tissue and Orgban Culture,* 47: 135–144, "A risk assessment study of plant genetic transformation using Agrobacterium and implications for analysis of transgenic plants".

Ejdeback, et al.—1997, *Protein Expression and Purification,* 11: 17–25, "Effects of Codon Usage and Vector—Host Combinations on the Expression of Spinach Plastocyanin in *Escherichia coli*".

Mehta, et al.—1997, *Protein Expression and Purification,* 11: 86–94, "Optimized Gene Synthesis, High Level Expression, Isotopic Enrichment, and Refolding of Human Interleukin–5".

\* cited by examiner

GENE ENCODING OXALATE DECARBOXYLASE FROM *ASPERGILLUS PHOENICES*

This application is a divisional of application Ser. No. 08/821,827, filed Mar. 21, 1997, pending.

FIELD OF THE INVENTION

This invention relates to a novel nucleic acid sequence encoding oxalate decarboylyase isolated from *Aspergillus phoenices* and to use of the nucleic acid sequence to produce its encoded protein.

BACKGROUND OF THE INVENTION

Oxalic acid (oxalate) is a diffusable toxin associated with various plant diseases, particularly those caused by fungi. Some leafy green vegetables, including spinach and rhubarb, produce oxalate as a nutritional stress factor. When plants containing oxalate are consumed in large amounts, they can be toxic to humans.

Oxalate is used by pathogens to gain access into and subsequently throughout an infected plant. See for example, Mehta and Datta, *The Journal of Biological Chemistry*, 266:23548–23553, 1991; and published PCT Application WO92/14824.

Field crops such as sunflower, bean, canola, alfalfa, soybean, flax, safflower, peanut, clover, as well as numerous vegetable crops, flowers, and trees are susceptible to oxalate-secreting pathogens. For example, fungal species including Sclerotinia and Sclerotium use oxalic acid to provide an opportunistic route of entry into plants, causing serious damage to crops such as sunflower.

Because of the role of oxalate in plant disease and toxicity, compounds that inhibit oxalate mediated disease, and particularly genes encoding such inhibitory degrading molecules, are greatly needed.

Enzymes that utilize oxalate as a substrate have been identified. These include oxalate oxidase and oxalate decarboxylase. Oxalate oxidase catalyzes the conversion of oxalate to $CO_2$ and $H_2O_2$. A gene encoding barley oxalate oxidase has been cloned from a barley root cDNA library and sequenced (See PCT publication No. WO92/14824). A gene encoding wheat oxalate oxidase activity (Germin) has been isolated and sequenced, (PCT publication No. WO 94/13790) and the gene has been introduced into a canola variety. Canola plants harboring the gene appeared to show some resistance to *Sclerotinia sclerotiorum*, in vitro (Dumas, et al., 1994, Abstracts: 4th Int'l. *Congress of Plant Molecular Biology*, #1906).

Oxalate decarboxylase converts oxalate to $CO_2$ and formic acid. A gene encoding oxalate decarboxylase has been isolated from *Collybia velutipes* (now termed *Flammulina velutipes*) and the cDNA clone has been sequenced (WO94/12622, published Jun. 9, 1994). Oxalate decarboxylase activities have also been described in *Aspergillus niger* and *Aspergillus phoenices* (Emiliani et al., 1964, *ARCH. Biochem. Biophys.* 105:488–493), however the amino acid sequence and nucleic acid sequence encoding these enzyme activities have not been isolated or characterized.

Enzymatic assays for clinical analysis of urinary oxalate provide significant advantages in sensitivity and qualification Obzansky, et al., 1983, *Clinical Chem.* 29:1815–1819. For many reasons, including reactivity with interfering analytes and the high cost of available oxalate oxidase used in this diagnostic assay, alternative enzymes are needed. (Lathika et al., 1995, *Analytical Letters* 28: 425–442).

In this application, we disclose the isolation, cloning, and sequencing of a unique gene encoding an oxalate decarboxylase enzyme from *Aspergillus phoenices*. The gene is useful in producing highly purified *Aspergillus phoenices* oxalate decarboxylase enzyme, in producing transonic plant cells and plants expressing the enzyme in vivo, and in diagnostic assays of oxalate.

SUMMARY OF THE INVENTION

The present invention provides a nucleic acid sequence encoding oxalate decarboxylase isolated from *Aspergillus phoenices* (APOXD). The gene sequence [Seq ID No:1], the recombinant protein produced therefrom [Seq ID No:2], and vectors, transformed cells, and plants containing the gene sequence are provided as individual embodiments of the invention, as well as methods using the gene or its encoded protein. The nucleic acid is useful for producing oxalate decarboxylase for commercial applications, including degradation of oxalic acid, protection against oxalic acid toxicity, and diagnostic assays to quantify oxalate.

The nucleic acid of the invention is also useful as a selectable marker. Growth of plant cells in the presence of oxalic acid favors survival of plant cells transformed with the coding sequence of the gene.

The present invention also includes compositions and methods for degrading oxalic acid, in providing protection against oxalic acid toxicity, and in combating and providing protection against plant pathogens that utilize oxalate to gain access to plant tissue or otherwise in the course of the pathogenesis of the disease. Oxalate decarboxylase from *Aspergillis phoenices* (APOXD) of the present invention is combined with an appropriate carrier for delivery to the soil or plants. Alternatively, plant cells are transformed with the nucleic acid sequence of the invention for expression of APOXD in vivo.

DETAILED DESCRIPTION OF THE INVENTION

Figure 1:
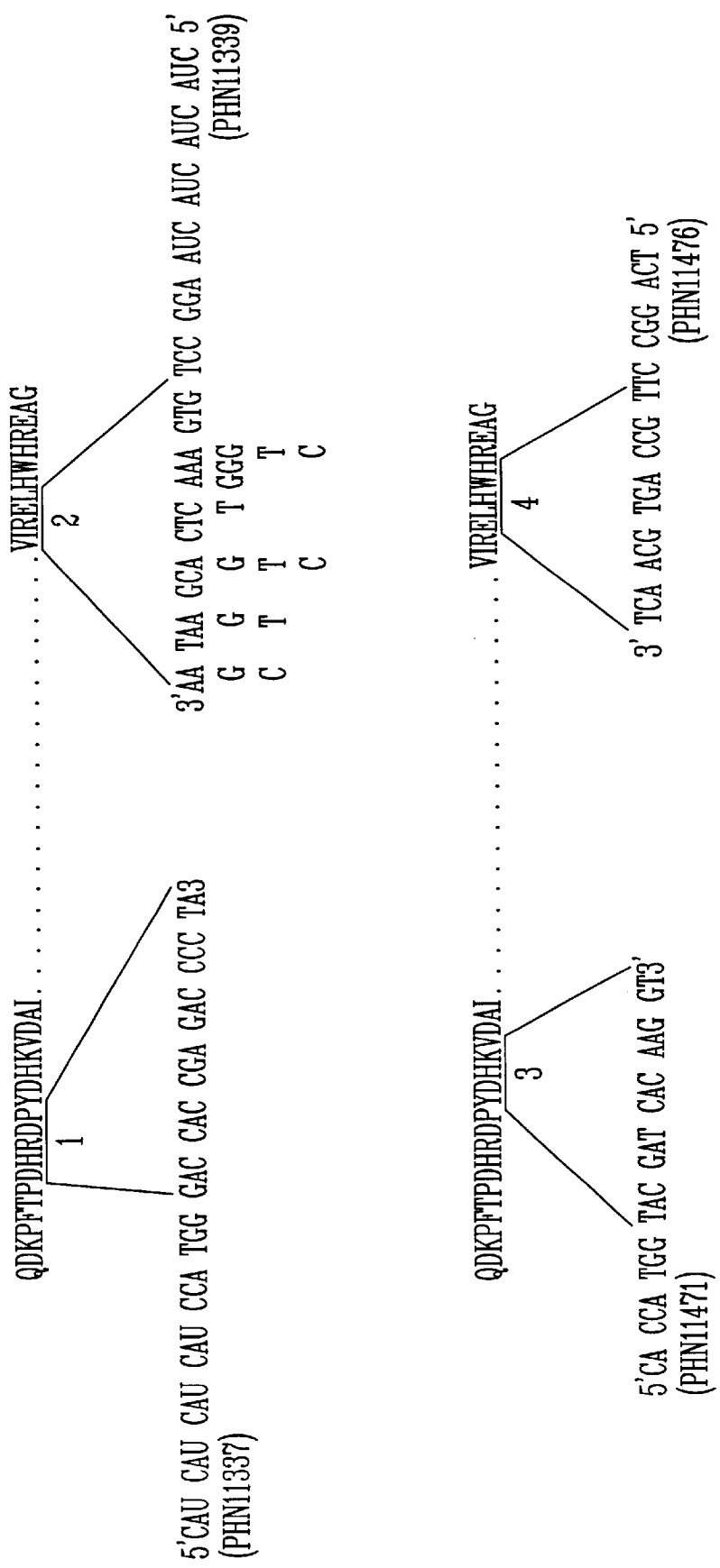
FIG. 1 is a diagram showing a first primer strategy for amplification of a portion of the nucleic acid sequence encoding APOXD.

The purified oxalate decarboxylase of the present invention has many commercial uses, including inhibiting oxalate toxicity of plants and preventing pathogenic disease in plants where oxalic acid plays a critical role. It has been suggested that degradation of oxalic acid is a preventative measure, e.g., to prevent invasion of a pathogen into a plant, or during pathogenesis, when oxalic acid concentrations rise (Dumas, et al., 1994, Supra). The gene of the invention is also useful as a selectable marker of transformed cells, for diagnostic assay of oxalate, and for production of the enzyme in plants.

Nucleic Acid Sequence Encoding APOXD

A nucleic acid sequence encoding APOXD [Seq. ID No: 1] has now been determined by methods described more fully in the Examples below. Briefly, DNA encoding APOXD was obtained by amplification of genomic *A. phoenices* DNA using a RACE strategy as described in Innis et. al., eds., 1990, *PCR Protocols. A Guide to Methods and Applications,* Academic Press, San Diego, Calif., pages 28–38. See also pages 39–45, "Degenerate primers". The nucleic acid sequence and its deduced amino acid sequence [Seq. ID No:2] are shown below in Table 1. The predicted signal peptide [Seq. ID No: 3] and pre-protein [Seq. ID No: 4] are shown along with the potential cleavage site between them as determined by computer analysis; using PC gene software (IntelliGenetics, Inc., Mountain View, Calif.). The mature protein [Seq. ID No: 5] is also indicated. This 1.4 kb sequence encodes a 458 amino acid enzyme subunit with a calculated molecular weight of 51,994 daltons. Southern hybridization indicates that the enzyme is encoded by a single gene in the *Aspergillis phoenices* genome. The plasmid pPHP9685 containing the nucleic acid sequence encoding APOXD as an insert was deposited with the A.T.C.C. on Mar. 18, 1997, having Accession No. 97959.

TABLE 1

SEQUENCE OF FULL LENGTH APOXD DNA

```
                              |Signal Peptide
GGCTTGTCAG GATCCTTCCA AAG     |ATG CAG CTA ACC CTG CCA CCA CGT CAG CTG     53
                              |Met Gln Leu Thr Leu Pro Pro Arg Gln Leu
                              | 1                 5                  10

TTG CTG AGT TTC GCG ACC GTG GCC GCC CTC CTT GAT CCA AGC CAT GGA            101
Leu Leu Ser Phe Ala Thr Val Ala Ala Leu Leu Asp Pro Ser His Gly
                15                  20                  25

|Pre-protein
|GGC CCG GTC CCT AAC GAA GCG TAC CAG CAA CTA CTG CAG ATT CCC GCC          149
|Gly Pro Val Pro Asn Glu Ala Tyr Gln Gln Leu Leu Gln Ile Pro Ala
|30                  35                  40

|Mature protein
TCA TCC CCA TCC ATT TTC TTC     |CAA GAC AAG CCA TTC ACC CCC GAT CAT       197
Ser Ser Pro Ser Ile Phe Phe     |Gln Asp Lys Pro Phe Thr Pro Asp His
        45                      |50                  55

NruI
CGC GAC CCC TAT GAT CAC AAG GTG GAT GCG ATC GGG GAA GGC CAT GAG            245
Arg Asp Pro Tyr Asp His Lys Val Asp Ala Ile Gly Glu Gly His Glu
        60                  65                  70

CCC TTG CCC TGG CGC ATG GGA GAT GGA GCC ACC ATC ATG GGA CCC CGC            293
Pro Leu Pro Trp Arg Met Gly Asp Gly Ala Thr Ile Met Gly Pro Arg
75                  80                  85                  90

AAC AAG GAC CGT GAG CGC CAG AAC CCC GAC ATG CTC CGT CCT CCG AGC            341
Asn Lys Asp Arg Glu Arg Gln Asn Pro Asp Met Leu Arg Pro Pro Ser
                95                  100                 105

ACC GAC CAT GGC AAC ATG CCG AAC ATG CGG TGG AGC TTT GCT GAC TCC            389
Thr Asp His Gly Asn Met Pro Asn Met Arg Trp Ser Phe Ala Asp Ser
            110                 115                 120

CAC ATT CGC ATC GAG GAG GGC GGC TGG ACA CGC CAG ACT ACC GTA CGC            437
His Ile Arg Ile Glu Glu Gly Gly Trp Thr Arg Gln Thr Thr Val Arg
            125                 130                 135

GAG CTG CCA ACG AGC AAG GAG CTT GCG GGT GTA AAC ATG CGC CTC GAT            485
Glu Leu Pro Thr Ser Lys Glu Leu Ala Gly Val Asn Met Arg Leu Asp
        140                 145                 150

GAG GGT GTC ATC CGC GAG TTG CAC TGG CAT CGA GAA GCA GAG TGG GCG            533
Glu Gly Val Ile Arg Glu Leu His Trp His Arg Glu Ala Glu Trp Ala
155                 160                 165                 170

TAT GTG CTG GCC GGA CGT GTA CGA GTG ACT GGC CTT GAC CTG GAG GGA            581
Tyr Val Leu Ala Gly Arg Val Arg Val Thr Gly Leu Asp Leu Glu Gly
                175                 180                 185

GGC AGC TTC ATC GAC GAC CTA GAA GAG GGT GAC CTC TGG TAC TTC CCA            629
Gly Ser Phe Ile Asp Asp Leu Glu Glu Gly Asp Leu Trp Tyr Phe Pro
            190                 195                 200

TCG GGC CAT CCC CAT TCG CTT CAG GGT CTC AGT CCT AAT GGC ACC GAG            677
Ser Gly His Pro His Ser Leu Gln Gly Leu Ser Pro Asn Gly Thr Glu
            205                 210                 215

TTC TTA CTG ATC TTC GAC GAT GGA AAC TTT TCC GAG GAG TCA ACG TTC            725
```

TABLE 1-continued

SEQUENCE OF FULL LENGTH APOXD DNA

| | | | | | | | | | | | | | | | |
|---|---|---|---|---|---|---|---|---|---|---|---|---|---|---|---|
| Phe | Leu | Leu | Ile | Phe | Asp | Asp | Gly | Asn | Phe | Ser | Glu | Glu | Ser | Thr | Phe |
| | | 220 | | | | 225 | | | | 230 | | | | | |

| | | | | | | | | | | | | | | |
|---|---|---|---|---|---|---|---|---|---|---|---|---|---|---|
| TTG | TTG | ACC | GAC | TGG | ATC | GCA | CAT | ACA | CCC | AAG | TCT | GTC | CTC | GCC | GGA | 773 |
| Leu | Leu | Thr | Asp | Trp | Ile | Ala | His | Thr | Pro | Lys | Ser | Val | Leu | Ala | Gly |
| 235 | | | | | 240 | | | | | 245 | | | | | 250 |

| AAC | TTC | CGC | ATG | CGC | CCA | CAA | ACA | TTT | AAG | AAC | ATC | CCA | CCA | TCT | GAA | 821 |
| Asn | Phe | Arg | Met | Arg | Pro | Gln | Thr | Phe | Lys | Asn | Ile | Pro | Pro | Ser | Glu |
| | | | | 255 | | | | | 260 | | | | | 265 | |

| AAG | TAC | ATC | TTC | CAG | GGC | TCT | GTC | CCA | GAC | TCT | ATT | CCC | AAA | GAG | CTC | 869 |
| Lys | Tyr | Ile | Phe | Gln | Gly | Ser | Val | Pro | Asp | Ser | Ile | Pro | Lys | Glu | Leu |
| | | | 270 | | | | | 275 | | | | | 280 | | |

| CCC | CGC | AAC | TTC | AAA | GCA | TCC | AAG | CAG | CGC | TTC | ACG | CAT | AAG | ATG | CTC | 917 |
| Pro | Arg | Asn | Phe | Lys | Ala | Ser | Lys | Gln | Arg | Phe | Thr | His | Lys | Met | Leu |
| | | 285 | | | | | 290 | | | | | 295 | | | |

| GCT | CAA | AAA | CCC | GAA | CAT | ACC | TCT | GGC | GGA | GAG | GTG | CGC | ATC | ACA | GAC | 965 |
| Ala | Gln | Lys | Pro | Glu | His | Thr | Ser | Gly | Gly | Glu | Val | Arg | Ile | Thr | Asp |
| | | 300 | | | | | 305 | | | | | 310 | | | |

| TCG | TCC | AAC | TTT | CCC | ATC | TCC | AAG | ACG | GTC | GCG | GCC | GCC | CAC | CTG | ACC | 1013 |
| Ser | Ser | Asn | Phe | Pro | Ile | Ser | Lys | Thr | Val | Ala | Ala | Ala | His | Leu | Thr |
| 315 | | | | | 320 | | | | | 325 | | | | | 330 |

| ATT | AAC | CCG | GGT | GCT | ATC | CGG | GAG | ATG | CAC | TGG | CAT | CCC | AAT | GCG | GAT | 1061 |
| Ile | Asn | Pro | Gly | Ala | Ile | Arg | Glu | Met | His | Trp | His | Pro | Asn | Ala | Asp |
| | | | 335 | | | | | 340 | | | | | 345 | | |

| GAA | TGG | TCC | TAC | TTT | AAG | CGC | GGT | CGG | GCG | CGA | GTG | ACT | ATC | TTC | GCT | 1109 |
| Glu | Trp | Ser | Tyr | Phe | Lys | Arg | Gly | Arg | Ala | Arg | Val | Thr | Ile | Phe | Ala |
| | | | 350 | | | | | 355 | | | | | 360 | | |

| GCT | GAA | GGT | AAT | GCT | CGT | ACG | TTC | GAC | TAC | GTA | GCG | GGA | GAT | GTG | GGC | 1157 |
| Ala | Glu | Gly | Asn | Ala | Arg | Thr | Phe | Asp | Tyr | Val | Ala | Gly | Asp | Val | Gly |
| | | 365 | | | | | 370 | | | | | 375 | | | |

| ATT | GTT | CCT | CGC | AAC | ATG | GGT | CAT | TTC | ATT | GAG | AAC | CTT | AGT | GAT | GAC | 1205 |
| Ile | Val | Pro | Arg | Asn | Met | Gly | His | Phe | Ile | Glu | Asn | Leu | Ser | Asp | Asp |
| | | 380 | | | | | 385 | | | | | 390 | | | |

| GAG | GAG | GTC | GAG | GTG | TTG | GAA | ATC | TTC | CGG | GCG | GAC | CGA | TTC | CGG | GAC | 1253 |
| Glu | Glu | Val | Glu | Val | Leu | Glu | Ile | Phe | Arg | Ala | Asp | Arg | Phe | Arg | Asp |
| 395 | | | | | 400 | | | | | 405 | | | | | 410 |

| TTT | TCT | TTG | TTC | CAG | TGG | ATG | GGA | GAG | ACG | CCG | CAG | CGG | ATG | GTG | GCA | 1301 |
| Phe | Ser | Leu | Phe | Gln | Trp | Met | Gly | Glu | Thr | Pro | Gln | Arg | Met | Val | Ala |
| | | | 415 | | | | | 420 | | | | | 425 | | |

| GAG | CAT | GTG | TTT | AAG | GAT | GAT | CCA | GAT | GCG | GCC | AGG | GAG | TTC | CTT | AAG | 1349 |
| Glu | His | Val | Phe | Lys | Asp | Asp | Pro | Asp | Ala | Ala | Arg | Glu | Phe | Leu | Lys |
| | | | 430 | | | | | 435 | | | | | 440 | | |

| AGT | GTG | GAG | AGT | GGG | GAG | AAG | GAT | CCA | ATT | CGG | AGC | CCA | AGT | GAG | | 1394 |
| Ser | Val | Glu | Ser | Gly | Glu | Lys | Asp | Pro | Ile | Arg | Ser | Pro | Ser | Glu | |
| | | 445 | | | | | 450 | | | | | 455 | | | |

| Stop |
| TAGATGA GGTTCTACGC GTGTATTTTG CTGATATCAT CGAAGCC | 1438 |

| APOXD Sequence | Nucleotides | Amino Acids | Seq. ID No. |
|---|---|---|---|
| 1.4 kb gene | 1–1437 | | 1 |
| Encoded Protein | 24–1397 | 1–458 | 2 |
| Signal Peptide | 24–101 | 1–26 | 3 |
| Pre-protein | 102–1397 | 27–458 | 4 |
| Mature Protein | 71–1394 | 50–457 | 5 |

Redundancy in the genetic code permits variation in the gene sequences shown in Table 1. In particular, one skilled in the art will recognize specific codon preferences by a specific host species and can adapt the disclosed sequence as preferred for the desired host. For example, rare codons having a frequency of less than about 20% in known sequence of the desired host are preferably replaced with higher frequency codons. Codon preferences for a specific organism may be calculated, for example, codon usage tables available on the INTERNET at the following address:

http://www.dna.affrc.go.jp/~nakamura/codon.html. One specific program available for Arabidopsis is found at: http://genome-www.stanford.edu/Arabidopsis/codon_usage.html.

Additional sequence modifications are known to enhance protein expression in a cellular host. These include elimination of sequences encoding spurious polyadenylation signals, exon/intron splice site signals, transposon-like repeats, and other such well-characterized sequences which may be deleterious to gene expression. The G-C content of the sequence may be adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, 1989, *Mol Cell Biol.* 9:5073–5080.

In addition, the native APOXD gene or a modified version of the APOXD gene might be further optimized for expression by omitting the predicted signal and pre-sequence, replacing the signal sequence with another signal sequence, or replacing the signal and pre-sequence with another signal sequence. Any one of the possible APOXD gene variations may work best when combined with a specific promoter and/or termination sequence.

APOXD Protein

The recombinant APOXD protein produced from the disclosed nucleic acid sequence provides a substantially pure protein useful to degrade oxalate, particularly in applications where highly purified enzymes are required. The recombinant protein may be used in enzymatic assays of oxalate or added to compositions containing oxalate to induce oxalate degradation.

When used externally, the enzyme can be placed in a liquid dispersion or solution, or may be mixed with a carrier solid for application as a dust or powder. The particular method of application and carrier used will be determined by the particular plant and pathogen target. Such methods are known, and are described, for example, in U.S. Pat. No. 5,488,035 to Rao.

Gene Delivery

The nucleic acid sequence encoding APOXD may be delivered to plant cells for transient transfections or for incorporation into the plant's genome by methods know in the art. Preferably, the gene is used to stably transform plant cells for expression of the protein in vivo.

To accomplish such delivery, the gene containing the coding sequence for APOXD may be attached to regulatory elements needed for the expression of the gene in a particular host cell or system. These regulatory elements include, for example, promoters, terminators, and other elements that permit desired expression of the enzyme in a particular plant host, in a particular tissue or organ of a host such as vascular tissue, root, leaf, or flower, or in response to a particular signal.

Promoters

A promoter is a DNA sequence that directs the transcription of a structural gene, e.g., that portion of the DNA sequence that is transcribed into messenger RNA (mRNA) and then translated into a sequence of amino acids characteristic of a specific polypeptide. Typically, a promoter is located in the 5' region of a gene, proximal to the transcriptional start site. A promoter may be inducible, increasing the rate of transcription in response to an inducing agent. In contrast, a promoter may be constitutive, whereby the rate of transcription is not regulated by an inducing agent. A promoter may be regulated in a tissue-specific or tissue-preferred manner, such that it is only active in transcribing the operably linked coding region in a specific tissue type or types, such as plant leaves, roots, or meristem.

Inducible Promoters

An inducible promoter useful in the present invention is operably linked to a nucleotide sequence encoding APOXD. Optionally, the inducible promoter is operably linked to a nucleotide sequence encoding a signal sequence which is operably linked to a nucleotide sequence encoding APOXD. With an inducible promoter, the rate of transcription increases in response to an inducing agent.

Any inducible promoter can be used in the present invention to direct transcription of APOXD, including those described in Ward, et al., 1993, *Plant Molecular Biol.* 22: 361:–366. Exemplary inducible promoters include that from the ACE1 system which responds to copper (Mett et al., 1993, *PNAS* 90: 4567–4571); In2 gene promoter from maize which responds to benzenesulfonamide herbicide safeners (Hershey et al., 1991, *Plant Mol. Biol.* 17:679–690; and the Tet repressor from Tn10 (Hersey, et al., 1991, *Mol. Gen. Genetics* 227:229–237; Gatz, et al., 1994, *Mol.Gen. Genetics* 243:32–38).

A particularly preferred inducible promoter is one that responds to an inducing agent to which plants do not normally respond. One example of such a promoter is the steroid hormone gene promoter. Transcription of the steroid hormone gene promoter is induced by glucocorticosteroid hormone. (Schena et al., 1991, *PNAS U.S.A.* 88:10421)

In the present invention, an expression vector comprises an inducible promoter operably linked to a nucleotide sequence encoding APOXD. The expression vector is introduced into plant cells and presumptively transformed cells are exposed to an inducer of the inducible promoter. The cells are screened for the presence of APOXD proteins by immunoassay methods or by analysis of the enzyme's activity.

Pathogen-Inducible Promoters

A pathogen-inducible promoter of the present invention is an inducible promoter that responds specifically to the inducing agent, oxalic acid, or to plant pathogens such as oxalic acid-producing pathogens including *Sclerotinia sclerotiorum*. Genes that produce transcripts in response to Sclerotinia and oxalic acid have been described in Mouley et al., 1992, *Plant Science* 85:51–59. One member of the prp1-1 gene family contains a promoter that is activated in potato during early stages of late blight infection and is described in Martini et al., 1993, *Mol. Gen.Genet.* 236:179–186.

Tissue-specific or Tissue-Preferred Promoters

A tissue specific promoter of the invention is operably linked to a nucleotide sequence encoding APOXD. Optionally, the tissue-specific promoter is operably linked to a nucleotide sequence encoding a signal sequence which is operably linked to a nucleotide sequence encoding APOXD. Plants transformed with a gene encoding APOXD operably linked to a tissue specific promoter produce APOXD protein exclusively, or preferentially, in a specific tissue.

Any tissue-specific or tissue-preferred promoter can be utilized in the instant invention. Examples of such promoters include a root-preferred promoter such as that from the phaseolin gene as described in Murai et al., 1983, *Science* 222:476–482 and in Sengupta-Gopalan et al., 1985, *PNAS USA* 82:3320–3324; a leaf-specific and light-induced promoter such as that from cab or rubisco as described in Simpson et al., 1985, *EMBO J.* 4(11):2723–2729, and in Timko et al., 1985, *Nature* 318:579–582; an anther-specific promoter such as that from LAT52 as described in Twell et al., 1989, *Mol. Gen. Genet.* 217:240–245; a pollen-specific promoter such as that from Zm13 as described in Guerrero et al., 1990, *Mol. Gen. Genet.* 224:161–168; and a microspore-preferred promoter such as that from apg as described in Twell et al., 1993, *Sex. Plant Reprod.* 6:217–224.

Other tissue-specific promoters useful in the present invention include a phloem-preferred promoter such as that associated with the Arabidopsis sucrose synthase gene as described in Martin et al., 1993, *The Plant Journal* 4(2): 367–377; a floral-specific promoter such as that of the Arabidopsis HSP 18.2 gene described in Tsukaya et al., 1993, *Mol.Gen. Genet.* 237:26–32 and of the Arabidopsis HMG2 gene as described in Enjuto et al., 1995, *Plant Cell* 7:517–527.

An expression vector of the present invention comprises a tissue-specific or tissue-preferred promoter operably linked to a nucleotide sequence encoding APOXD. The expression vector is introduced into plant cells. The cells are screened for the presence of APOXD protein by immunological methods or by analysis of enzyme activity.

Constitutive Promoters

A constitutive promoter of the invention is operably linked to a nucleotide sequence encoding APOXD. Optionally, the constitutive promoter is operably linked to a nucleotide sequence encoding a signal sequence which is operably linked to a nucleotide sequence encoding APOXD.

Many different constitutive promoters can be utilized in the instant invention to express APOXD. Examples include promoters from plant viruses such as the 35S promoter from cauliflower mosaic virus (CaMV), as described in Odell et al., 1985, *Nature* 313:810–812, and promoters from genes such as rice actin (McElroy et al., 1990, *Plant Cell* 2:163–171); ubiquitin (Christensen et al., 1989, *Plant Mol. Biol.* 12:619–632; and Christensen et al., 1992, *Plant Mol. Biol* 18:675–689); pEMU (Last et al., 1991, *Theor. Appl. Genet.* 81:581–588); MAS (Velten et al., 1984, *EMBO J.* 3:2723–2730); and maize H3 histone (Lepetit et al., 1992, *Mol.Gen.Genet.* 231:276–285; and Atanassvoa et al., 1992, *Plant Journal* 2(3):291–300).

The ALS promoter, a Xba/NcoI fragment 5' to the *Brassica napus* ALS3 structural gene, or a nucleotide sequence having substantial sequence similarity to the XbaI/NcoI fragment, represents a particularly useful constitutive promoter, and is described in published PCT Application number WO 96/30530.

In the present invention, an expression vector comprises a constitutive promoter operably linked to a nucleotide sequence encoding APOXD. The expression vector is introduced into plant cells and presumptively transformed cells are screened for the presence of APOXD proteins by immunoassay methods or by analysis of the enzyme's activity.

Additional regulatory elements that may be connected to the APOXD nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements of the APOXD gene are known, and include, but are not limited to, 3'termination and/or polyadenylation regions such as those of the *Agrobacterium tumefaciens* nopaline synthase (nos) gene (Bevan et al., 1983, *Nucl. Acids Res.* 11(2):369–385); the potato proteinase inhibitor II (PINII) gene (Keil. et al., 1986, *Nucl. Acids Res.* 14:5641–5650; and An et al., 1989, *Plant Cell* 1:115–122); and the CaMV 19S gene (Mogen et al., 1990, *Plant Cell* 2:1261–1272).

Plant signal sequences, including, but not limited to, signal-peptide encoding DNA/RNA sequences which target proteins to the extracellular matrix of the plant cell (Dratewka-Kos, et al., *J. Biol. Chem.* 264:4896–4900, 1989) and the Nicotiana plumbaginifolia extensin gene (DeLoose, et al., *Gene* 99:95–100, 1991), or signal peptides which target proteins to the vacuole like the sweet potato sporamin gene (Matsuoka, et al., *PNAS* 88:834, 1991) and the barley lectin gene (Wilkins, et al., *Plant Cell,* 2:301–313, 1990), or signals which cause proteins to be secreted such as that of PRIb (Lund, et al., *Plant Mol. Biol.* 18:47–53, 1992), or those which target proteins to the plastids such as that of rapeseed enoyl-Acp reductase (Verwoert, et al., *Plant Mol. Biol.* 26:189–202, 1994) are useful in the invention.

Gene Transformation Methods

Numerous methods for introducing foreign genes into plants are known and can be used to insert the APOXD gene into a plant host, including biological and physical plant transformation protocols. See, for example, Miki et al., 1993, "Procedure for Introducing Foreign DNA into Plants" in: *Methods in Plant Molecular Biology and Biotechnology,* Glick and Thompson, eds., CRC Press, Inc., Boca Raton, pages 67–88. The methods chosen vary with the host plant, and include chemical transfection methods such as calcium phosphate, microorganism-mediated gene transfer such as Agrobacterium (Horsch, et al., *Science* 227:1229–31, 1985), electroporation, micro-injection, and biolistic bombardment.

Expression cassettes and vectors and in vitro culture methods for plant cell or tissue transformation and regeneration of plants are known and available. See, for example, Gruber, et al., 1993, "Vectors for Plant Transformation" In: *Methods in Plant Molecular Biology and Biotechnology,* Glick and Thompson, eds., CRC Press, Inc., Boca Raton, pages 89–119.

Agrobacterium-mediated Transformation

The most widely utilized method for introducing an expression vector into plants is based on the natural transformation system of Agrobacterium. *A. tumefaciens* and *A. rhizogenes* are plant pathogenic soil bacteria which genetically transform plant cells. The Ti and Ri plasmids of *A. tumefaciens* and *A. rhizogenes,* respectfully, carry genes responsible for genetic transformation of plants. See, for example, Kado, 1991, *Crit. Rev.Plant Sci.* 10(1):1–32. Descriptions of the Agrobacterium vector systems and methods for Agrobacterium-mediated gene transfer are provided in Gruber et al., supra; Miki, et al., supra; and Moloney, et al., 1989, *Plant Cell Reports* 8:238.

Direct Gene Transfer

Despite the fact that the host range for Agrobacterium-mediated transformation is broad, some major cereal crop species and gymnosperms have generally be recalcitrant to this mode of gene transfer, even though some success has recently been achieved in rice (Hiei et al., 1994, *The Plant Journal* 6(2):271–282). Several methods of plant transformation, collectively referred to as direct gene transfer, have been developed as an alternative to Agrobacterium-mediated transformation.

A generally applicable method of plant transformation is microprojectile-mediated transformation, where DNA is carried on the surface of microprojectiles measuring about 1 to 4 Tm. The expression vector is introduced into plant tissues with a biolistic device that accelerates the microprojectiles to speeds of 300 to 600 m/s which is sufficient to penetrate the plant cell walls and membranes. (Sanford et al., 1987, *Part.Sci. Technol* 5:27; Sanford, 1988, *Trends Biotech* 6:299; Sanford, 1990, *Physiol. Plant* 79:206; Klein et al., 1992, *Biotechnology* 10:268)

Another method for physical delivery of DNA to plants is sonication of target cells as described in Zhang et al., 1991, *Bio/Technology* 9:996. Alternatively, liposome or spheroplast fusions have been used to introduce expression vectors into plants. See, for example, Deshayes et al., 1985, *EMBO J.* 4:2731–2737; and Christou, et al., 1987, *PNAS USA* 84:3962–3966. Direct uptake of DNA into protoplasts using CaCl$_2$ precipitation, polyvinyl alcohol or poly-L-ornithine have also been reported. See, for example, Hain et al., 1985, *Mol. Gen.Genet.* 199:161; and Draper, et al., 1982, *Plant & Cell Physiol.* 23:451.

Electroporation of protoplasts and whole cells and tissues has also been described. See, for example, D'Halluin, et al., 1992, *Plant Cell* 4:1495–1505; and Spencer, et al., 1994, *Plant Mol.Biol.* 24:51–61.

Particle Wounding/Agrobacterium Delivery

Figure 5:
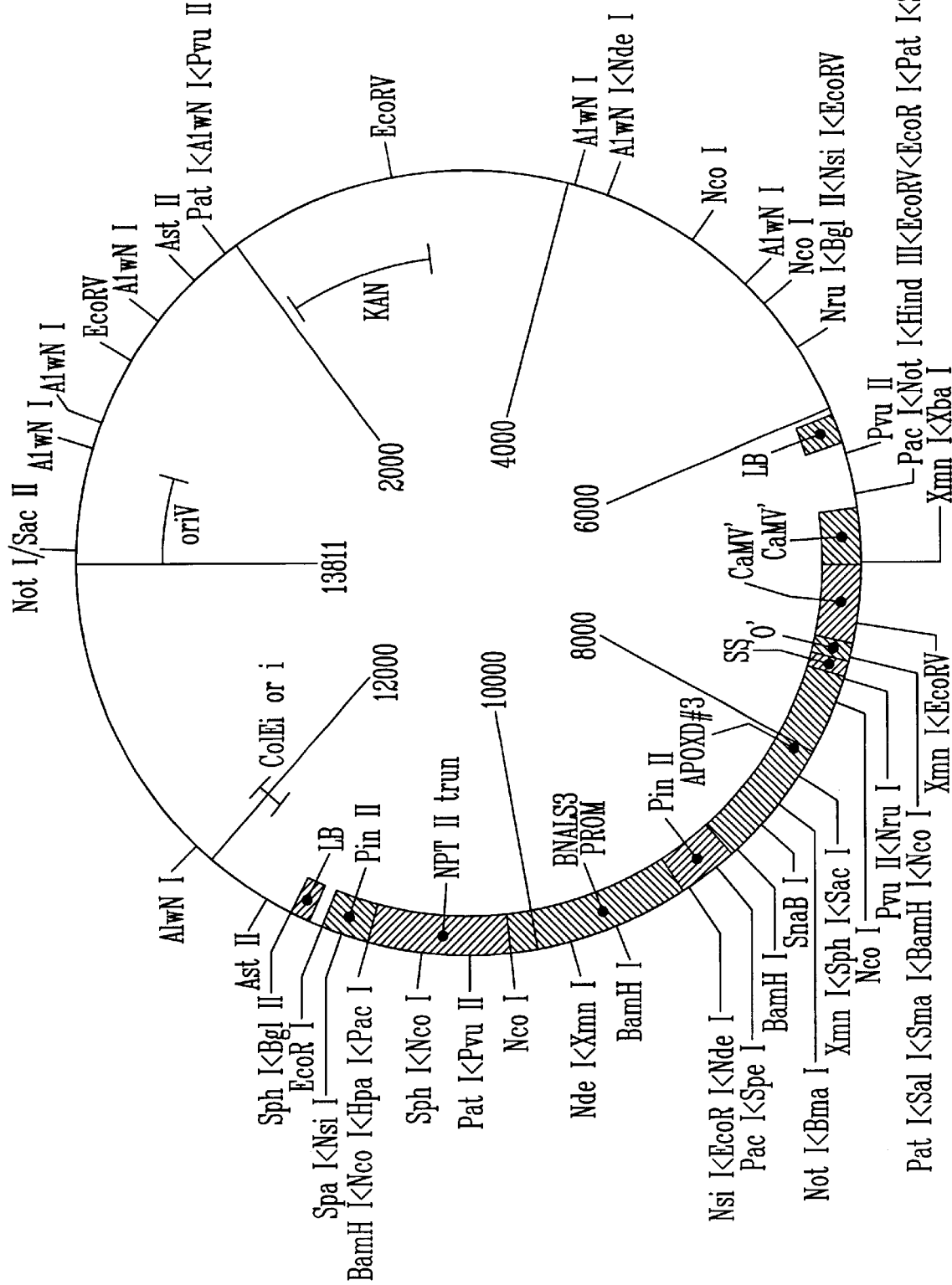
FIG. 5 is a diagram showing the plasmid pPHP9762 containing the nucleic acid sequence encoding APOXD with the fungal leader and pre-sequence replaced by the plant signal sequence of the wheat oxalate oxidase gene, Germin.

Another useful basic transformation protocol involves a combination of wounding by particle bombardment, followed by use of Agrobacterium for DNA delivery, as described by Bidney, et al. 1992, *Plant Mol. Biol.* 18:301–313. Useful plasmids for plant transformation include pPHP9762 shown in FIG. 5. The binary backbone for pPHP9762 is pPHP6333. See Bevan, 1984, *Nucleic Acids Research* 12:8711–8721. This protocol is preferred for transformation of sunflower plants, and employs either the "intact meristem" method or the "split meristem" method.

In general, the intact meristem transformation method (Bidney, et al., Supra) involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with Agrobacteriurn. To start the co-cultivation for intact meristems, Agrobacterium is placed on the meristem. After about a 3-day co-cultivation period the meristems are transferred to culture medium with cefotaxime (plus kanamycin for the NPTII selection). Selection can also be done using kanamycin.

The split meristem method involves imbibing seed, breaking of the cotyledons to produce a clean fracture at the plane of the embryonic axis, excising the root tip and then bisecting the explants longitudinally between the primordial leaves (Malone-Schoneberg et al., 1994, *Plant Science* 103:199–207). The two halves are placed cut surface up on the medium then bombarded twice with particles, followed by co-cultivation with Agrobacterium. For split meristems, after bombardment the meristems are placed in an Agrobacterium suspension for 30 minutes. They are then removed from the suspension onto solid culture medium for three day co-cultivation. After this period, the meristems are transferred to fresh medium with cefotaxime (plus kanamycin for selection).

Transfer by Plant Breeding

Alternatively, once a single transformed plant has been obtained by the foregoing recombinant DNA method, conventional plant breeding methods can be used to transfer the structural gene and associated regulatory sequences via crossing and backcrossing. Such intermediate methods will comprise the further steps of: (1) sexually crossing the disease-resistant plant with a plant from the disease-susceptible taxon; (2) recovering reproductive material from the progeny of the cross; and (3) growing disease-resistant plants from the reproductive material. Where desirable or necessary, the agronomic characteristics of the susceptible taxon can be substantially preserved by expanding this method to include the further steps of repetitively: (1) backcrossing the disease-resistant progeny with disease-susceptible plants from the susceptible taxon; and (2) selecting for expression of APOXD activity (or an associated marker gene) among the progeny of the backcross, until the desired percentage of the characteristics of the susceptible taxon are present in the progeny along with the gene imparting APOXD activity.

By the term "taxon" herein is meant a unit of botanical classification of genus or lower. It thus includes genus, species, cultivars, varieties, variants and other minor taxonomic groups which lack a consistent nomenclature.

Assay Methods

Transgenic plant cells, callus, tissues, shoots, and transonic plants are tested for the presence of the APOXD gene by DNA analysis (Southern blot or PCR) and for expression of the gene by immunoassay or by assay of oxalate decarboxylase activity. Tolerance to exogenous oxalic acid can also be used as a functional test of enzyme expression in transformed plants.

APOXD ELISA

Transonic cells, callus, plants and the like are screened for the expression of APOXD protein by immunological assays, including ELISA. Anti-APOXD antibodies are generated against APOXD preparations by known methods and are used in typical ELISA reactions. Polyclonal anti-APOXD can, for example, detect a range of about 10–100 pg APOXD protein in transgenic plant tissues.

In a suitable method for an APOXD-ELISA assay, fresh leaf or callus tissue is homogenized and centrifuged. An aliquot of the supernatant is added to a microtiter plate with a first anti-APOXD antibody and incubated for sufficient time for antibody-antigen reaction. The bound antibody is then reacted with a second antibody linked to a marker, which marker is developed or otherwise converted to a detectable signal correlated to the amount of APOXD protein in the sample. Any of the known methods for producing antibodies and utilizing such antibodies in an immunoassay can be used to determine the amount of APOXD expressed in transgenic plant cells and tissues of the invention.

Oxalate Decarboxylase Assay

Transgenic cells, tissue, or plants expressing the APOXD gene are assayed for enzyme activity to verify expression of the gene. In general, the cells or tissue is frozen in liquid nitrogen, placed on a lyophilizer overnight to dehydrate, then crushed into a fine powder for use in the assay reaction. Leaf tissue is homogenized as fresh tissue in the reaction mixture, or dehydrated and treated as described above.

A typical assay reaction is begun by adding 0.75 mg of powdered tissue, such as callus, to 1 ml of oxalate decarboxylase reaction mixture: 900 Tl 0.2 M sodium phosphate buffer, pH 5.0, and 100 Tl of 10 mM sodium oxalate, pH 5.0. The reaction is incubated at room temperature for 3 hours with gentle mixing, and is stopped by the addition of 150 Tl of 1 M Tris-HCl, pH 7.0. The mixture is centrifuged, and an aliquot is placed in a cuvette with NAD (600 Tg) and formate dehydrogenase (200 Tg). The absorbance at 340 nm is correlated to the activity of the APOXD enzyme.

Use of Oxalate Decarboxylase as a Selectable Marker

Oxalate decarboxylase is useful in selecting successful transformants, e.g., as a selectable marker. Growth of plant cells in the presence of oxalic acid favors the survival of plant cells that have been transformed with a gene encoding an oxalate-degrading enzyme, such as APOXD. In published PCT application WO 94/13790, herein incorporated by reference, plant cells grown on a selection medium containing oxalic acid (and all of the elements necessary for multiplication and differentiation of plant cells) demonstrated selection of only those cells transformed with and expressing oxalate oxidase. In like manner, transformation and expression of the gene encoding APOXD in plant cells is used to degrade oxalic acid present in the media and allow the growth of only APOXD-gene transformed cells.

Production of APOXD in Plants

Trangenic plants of the present invention, expressing the APOXD gene, are used to produce oxalate decarboxylase in commercial quantities. The gene transformation and assay selection techniques described above yield a plurality of transgenic plants which are grown and harvested in a conventional manner. Oxalate decarboxylase is extracted from the plant tissue or from total plant biomass. Oxalate decarboxylase extraction from biomass is accomplished by known methods. See for example, Heney and Orr, 1981, Anal. Biochem. 114:92–96.

In any extraction methodology, losses of material are expected and costs of the procedure are also considered. Accordingly, a minimum level of expression of oxalate decarboxylase is required for the process to be deemed economically worthwhile. The terms "commercial" and "commercial quantities" here denote a level of expression where at least 0.1% of the total extracted protein is oxalate decarboxylase. Higher levels of oxalate decarboxylase expression are preferred.

Example 1

Cloning of the Gene Encoding APOXD

Protein Sequence

A commercial preparation of *A. phoenices* oxalate decarboxylase enzyme was obtained from Boehringer Mannheim. (Catalog #479 586) SDS polyacrylamide gel electrophoresis was used to determine the purity of the enzyme. Only one dark band appeared following Coomassie blue staining of the polyacrylamide gel (12.5%). This band was about 49 kd in size, as determined by comparison to molecular weight markers. Aliquots of the preparation were sent to the University of Michigan for sequence analysis by Edman degradation on an automated protein sequencer. Preparative polyacrylamide gels were run and the APOXD band was isolated from the gel prior to sequencing. The protein was first sequenced at the amino terminus. Proteins were chemically cleaved into fragments by cyanogen bromide, size separated on polyacrylamide gels, and isolated as bands on the gel for further preparation and sequencing. The results of the sequencing are shown below in Table 2.

TABLE 2

| Peptide | Sequence* | Seq. ID No. |
|---|---|---|
| amino terminus | Gln Asp Lys Pro Phe Thr Pro Asp His Arg Asp Pro Tyr Asp His Lys Val Asp Ala Ile Gly Glu X His Glu Pro Leu | 6 |
| fragment 1 | Val Ile Arg Glu Leu His Trp His Arg Glu Ala Gly | 7 |
| fragment 2 | Arg Leu Asp Glu Gly Val IIe Arg Glu Leu His Cys His Arg Glu Ala Glu | 8 |
| fragment 3 | Ser Tyr Phe Lys Arg Gly Arg Ala Arg Tyr Thr Ile Phe Ala Ala Glu Gly Asn Ala Arg | 9 |
| fragment 4 | Ser Ala His Thr Pro Pro Ser Val Leu Ala Gly Asn | 10 |

*X = Unknown.

Diagnostic Oxalate Assay

Clinical measurement of oxalic acid in urine is important, for example, in the diagnosis and treatment of patients with urinary tract disorders or hyperoxaluric syndromes. The recombinant APOXD enzyme of the invention is preferably immobilized onto beads or solid support, or added in aqueous solution to a sample for quantitation of oxalate. As discussed above, oxalate decarboxylase catalyze s the conversion of oxalate to $CO_2$ and formic acid. A variety of detection systems can be utilized to quantify this enzyme catalyzed conversion, including methods for detecting an increase in $CO_2$, or for detecting an increase in formic acid.

For example, the conversion of oxalate to formic acid and $CO_2$ is assayed by determining formate production via the reduction of NAD in the presence of formate dehydrogenase. This method is described in Lung, et al., 1994, *J. Bacteriology*, 176:2468–2472 and Johnson, et al., 1964, *Biochem. Biophys.* Acta 89:35.

A calibration curve is generated using known amounts of oxalic acid. The amount of oxalate in a specimen is extrapolated from the standard curve.

Other enzymatic assays and the like are adapted by known methods to utilize the APOXD enzyme to detect conversion of oxalate.

EXAMPLES

The invention is described more fully below in the following Examples, which are exemplary in nature and are not intended to limit the scope of the invention in any way.

PCR Amplification of Genomic *A. phoenices*

Genomic DNA was used as the PCR template to amplify the APOXD sequence. *Aspergillus phoenices* was obtained from the American Type Culture Collection (ATCC), Rockville, Md. Cultures were established on solid potato dextrose agar medium (Difco formulation). Liquid stationary cultures were started from culture plates by innoculatory spores in a minimal growth medium previously described for the culture of Aspergillus strains (Emiliani, et al., 1964, *Arch. Biochem. Biophys* 105:488–493, cited above).

To isolate DNA, mycelial mats were recovered from 4-day liquid stationary cultures, washed in cold water, and blotted dry. The tissue was then frozen in liquid nitrogen, ground by mortar and pestle, and stored frozen at –80° C. DNA was extracted by the method described for fungal mycelium in Sunis et al. (eds.), 1990, *PCR protocols*, pages 282–287.

PCR Strategy

As diagrammed in FIG. 1, primers were designed for both the N-terminal protein sequence and for an internal peptide fragment. One set of primers (PHN 11337 [Seq ID No. 11] and PHN 11339 [Seq ID No. 12]) was designed with nearly full degeneracy. A second set of primers (PHN 11471 [Seq. ID No. 13] and PHN 11476 [Seq ID No. 14]) was designed with no degeneracy. These were based on a codon usage table for *Aspergillus niger* generated using the Wisconsin Sequence Analysis Package (GCG) (Genetics Computer Group, Inc., Madison, Wis.). The sequences of these primers is shown in Table 3, below, and diagrammatically in FIG. 1.

Table 3 shows the degenerate primer mixtures using IUPAC designations, as described in Cornish-Bowden, 1985, *Nucleic Acids Res.* 13:3021–3030. The IUPAC nucleic acid symbols include: Y=C or T; N=A, T, C, or G; R=A or G; D=A, T, or G; and V=A, C, or G. Both of these PCR strategies were successful in amplifying a DNA fragment, shown in Table 4, having homology to the protein sequence data shown in Table 2.

TABLE 3

| Primer Sets (5'-3') | | Seq. ID # |
|---|---|---|
| CAU CAU CAU CAU CCA TGG GAY CAY CGN GAY CCY TA | PHN11337 | 11 |
| CUA CUA CUA CUA AGG CCT GTG NRR YTC NCG DAT VA | PHN11339 | 12 |
| CA CCA TGG TAC GAT CAC AAG GT | PHN11471 | 13 |
| TCA GGC CTT GCC AGT GCA ACT | PHN11476 | 14 |

PCR reactions were set up containing increasing quantities of *A. phoenices* genomic DNA, in the range of 1–10 nanograms, and various oligonucleotide primer sets. Degenerate primers were added at a ten-fold higher concentration than that standardly used, due to their degeneracy. All other conditions for PCR were standard, essentially as described in Innis, et al., 1990, *PCR Protocols,* pages 282–287, except for the annealing temperatures for the primers. These temperatures were determined on an individual basis using the Oligo 4.0 computer program for analysis as described in Rychlik et al., 1989, *Nuc.Acids Res.* 17:8543–8551. Specifically, the primers annealing temperatures were:

| primer | first 5 cycles | next 30 cycles |
|---|---|---|
| PHN 11337 | 54° C. | 60° C. |
| PHN 11339 | 54° C. | 60° C. |
| PHN 11471 | 50° C. | 58° C. |
| PHN 11476 | 50° C. | 58° C. |

Transformation and Sequencing

PCR amplification products were ligated into pCR II using the TA Cloning Kit (InVitrogen, San Diego, Calif.), and transformed into *E.coli* strain DH5α competent cells (Life Technologies, Gathersburg, Md.) according to the protocol provided with the strain, for cloning and sequencing. Transformed bacteria with plasmid insertions were selected on medium 34Z (LB agar plates containing 100 mg/l carbenicillin) using standard X-GAL selection protocols (Ausubel, et al., eds, 1989, *Current Protocols in Molecular Biology,* pages 1.0.3–1.15.8). Briefly, white colonies were picked with an inoculating loop and inoculated directly into a PCR reaction mixture containing primers specific to the universal and reverse promoter regions just outside the multiple cloning site. The remaining innoculum on the loop was used to streak a plate of 34Z medium and numbered to correspond to the PCR reaction. Successful amplification of an inserted PCR fragment resulted in a band on an ethidium bromide stained agaraose gel which was slightly larger than the size of the insert. Bacterial isolates with an insert of the correct size were inoculated into shaking liquid cultures and subsequently used for plasmid isolation protocols, followed by sequencing of the insert of interest.

Sequence quality plasmid was prepared by using the Nucleobond P-100 plasmid isolation kit (Machery-Nagle GmBH & Co., Cat.No. BP 101352 m distributed by the Nest Group, Southboro, Mass.). This kit uses an alkaline lysis step and is followed by an ion exchange silica column purification step. Plasmid and gene specific primers were sent to Iowa State University to be sequenced on an automated, ABI DNA Sequencing machine.

The degenerate primer PCR experiment resulted in the amplification of a 0.4 kb band, which was sequenced and determined to have a deduced amino acid sequence matching the protein data in Table 2. The non-degenerate primer experiment resulted in DNA fragments of various sizes. One fragment was about 0.4 kb in length and encoded a protein having homology to the protein sequence data of Table 2. The region of the APOXD gene that was amplified by both primer sets was nearly the same, so DNA sequence data for the amplified fragments was compiled, and the sequence of the compiled APOXD genomic fragment is shown in Table 4 (Seq ID No. 15) together with its deduced amino acid sequence (Seq ID No. 16). The underlined amino acid sequences were represented in the original protein sequence analysis data (Table 2).

TABLE 4

| APOXD FRAGMENT |
|---|

|  |  | 10 |  |  | 20 |  |  | 30 |  |  | 40 |  |  |
|---|---|---|---|---|---|---|---|---|---|---|---|---|---|
| AC | GAT | CAC | AAG | GTG | GAT | GCG | ATC | GGG | GAA | GGC | CAT | GAG | CCC | TTG | CCC |
|  | Asp | His | Lys | Val | Asp | Ala | Ile | Gly | Glu | Gly | His | Glu | Pro | Leu | Pro |

| 50 |  |  | 60 |  |  | 70 |  |  | 80 |  |  | 90 |  |  |
|---|---|---|---|---|---|---|---|---|---|---|---|---|---|---|
| TGG | CGC | ATG | GGA | GAT | GGA | GCC | ACC | ATC | ATG | GGA | CCC | CGC | AAC | AAG | GAC |
| Trp | Arg | Met | Gly | Asp | Gly | Ala | Thr | Ile | Met | Gly | Pro | Arg | Asn | Lys | Asp |

| 100 |  |  | 110 |  |  | 120 |  |  | 130 |  |  | 140 |  |
|---|---|---|---|---|---|---|---|---|---|---|---|---|---|
| CGT | GAG | CGC | CAG | AAC | CCC | GAC | ATG | CTC | CGT | CCT | CCG | AGC | ACC | GAC | CAT |
| Arg | Glu | Arg | Gln | Asn | Pro | Asp | Met | Leu | Arg | Pro | Pro | Ser | Thr | Asp | His |

| 150 |  |  | 160 |  |  | 170 |  |  | 180 |  |  | 190 |
|---|---|---|---|---|---|---|---|---|---|---|---|---|
| GGC | AAC | ATG | CCG | AAC | ATG | CGG | TGG | AGC | TTT | GCT | GAC | TCC | CAC | ATT | CGC |
| Gly | Asn | Met | Pro | Asn | Met | Arg | Trp | Ser | Phe | Ala | Asp | Ser | His | Ile | Arg |

| 200 | 210 | 220 | 230 | 240 |
|---|---|---|---|---|

TABLE 4-continued

APOXD FRAGMENT

```
ATC GAG GTA AGC CCT TCG AGG GTT TTG TGT ACG ACA AGC AAA ATA GGC
Ile Glu 250             260             270             280
TAA TGC ACT GCA GGAGGGC GGC TGG ACA CGC CAG ACT ACC GTA CGC GAG
                        Gly Trp Thr Arg Gln Thr Thr Val Arg Glu 290             300             310             320             330
CTG CCA ACG AGC AAG GAG CTT GCG GGT GTA AAC ATG CGC CTC GAT GAG
Leu Pro Thr Ser Lys Glu Leu Ala Gly Val Asn Met Arg Leu Asp Glu 340             350             360             370             380
GGT GTC ATC CGC GAG TTG CAC TGG CAA GGG CTG AAG GCG AAT TCC AGC
Gly Val Ile Arg Glu Leu His Trp 390             400             410             420             430
ACA CTG GCG GCC GTT ACT AGT GGA TCC GAG CTC GGT ACC AAG CTT GAT
GC ATAGCT
```

3' RACE

Figure 2:
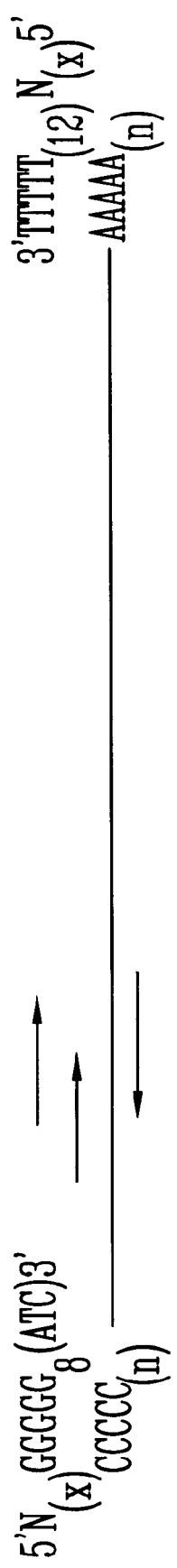
FIG. 2 is a diagram showing the primer position and design of nested, gene-specific primers (arrows above diagram) for 3' RACE and the single gene specific primer (arrow beneath diagram) used for 5' RACE.

Nested oligonucleotide primers were designed based on the genomic DNA sequence fragment which was previously amplified (Table 4) and used for 3' RACE to enhance gene specific amplification. The nested primer design is diagrammatically shown in FIG. 2 and the nucleic acid sequences of the primers is shown below in Table 5. Arrows represent the gene specific primers (from top to bottom) PHN 11811, PHN 11810, and the oligo dT based 3' primer from a commercial supplied 3' RACE kit (Life Technologies, Gaithersburg, Md., Cat. No. 18373-019)

5' RACE

Total RNA was reverse transcribed with commercially available components and a set of oligo dT-based primers ending in G, C or A which are collectively termed Bam T17V (5' CGC GGA TCC $GT_{17}$ V) 3') [Seq ID No. 19] These primers are disclosed in published PCT Application No. US96/08582. First strand cDNA was oligo dC-tailed and then column purified using commercially available components. (Life Technologies, Gaithersburg). The product of this reaction was then used in PCR with primer set Bam G13H, an equimolar mixture of oligo dG primers ending in A, C, or

TABLE 5

| 3' RACE Primers (5'-3') | Seq ID No. |
|---|---|
| PHN 11810 AAC ATG CGG TGG AGC TTT G | 17 |
| PHN 11811 CAU CAU CAU CAU CAT TCG CAT CGA GGT AAG | 18 |

The first round of PCR amplification using the outside gene specific primer (GSP) PHN11810 and the oligo dT based 3' primer resulted in no visible DNA bands. The inside GSP PHN11811 and the oligo dT based 3' primer were then used for a second round of amplification on the same sample. A large number of bands appeared, some of which stained intensely with ethidium bromide and some which did not. The prominent bands were 0.4, 0.8 and 1.3 kb in size. This experiment was set up using 5' and 3' primers with custom ends which only allow ligation of DNA fragments amplified by both. This method permitted the reaction to be used in the ligation protocol without further purification or characterization of the DNA fragments. All three of the prominent bands described above were ligated into pAMP1 (Life Technologies, Cat. No., 18384-016), transformed into DH5α cells (Life Technologies, Cat. No. 18263-12), cloned and sequenced. The 0.4 kb band was found to encode an amino acid sequence having homology to the APOXD sequence data of Table 1.

T (5' TAA GGA TCC TCC $TG_{13}H$ 3') [Seq. ID NO: 20], and a second gene specific primer, PHN 11813 [Seq ID No. 21]. Amplified products were characterized by Southern analysis using the protocol as described in Ausubel, et al. (eds.), 1989, *Current Protocols in Molecular Biology*, pages 2.0.1–2.12.5.

Hybridization of the 5' RACE product was done using the PCR amplified genomic DNA fragment (Table 4) as a radiolabeled probe. A 0.6 kb band was amplified by this reaction and was strongly labeled with the probe. No other bands appeared. This 0.6 kb band was ligated into the PCR II vector using the TA-cloning procedure, transformed into DH5I, cloned and sequenced. The DNA sequence analysis of the 0.6 kb PCR fragment showed it was homologous to the APOXD sequence data shown in Table 2.

TABLE 6

| 5' RACE Primers | SEQ. ID No. |
|---|---|
| Bam T17V 5' CGC GGA TCC $GT_{17}V$ 3' | 19 |
| Bam G13H 5' TAA GGA TCC $TG_{13}H$ 3' | 20 |
| PHN 11813 5' CAU CAU CAU CAU TAC CTC GAT GCG AAT GTG 3' | 21 |

IUPAC Symbols: V = G, C, or A; H = A, T, or C.

PCR For Full Length

The 5' and 3' RACE products were sequenced to their ends as determined by the initiating methionine and the poly-A tail respectively. DNA sequence at each end was analyzed by Oligo 4.0 for oligonucleotide primer design in preparation for PCR to obtain the complete gene.

Primer PHN 12566 designed to the 3' end of the sequence, was used to reverse transcribe total RNA. Primers PHN 12565 and PHN 12567 were used to amplify first strand cDNA. The PCR amplified band was ligated into PCR II using the TA cloning kit (In Vitrogen; San Diego, Calif.) then transformed into DH5I, cloned, and sequenced.

TABLE 7

| Full Length cDNA Primers (5'→3') | SEQ. ID No. |
|---|---|
| PHN 12566 CGA TGA TAT CAG CAA AAT ACA CGC GTA | 22 |
| PHN 12565 GTC AGG ATC CCG CTT CAT CCC CAT CC | 23 |
| PHN 12567 CAT GAT ATC CTA CTC ACT TGG GCT CCG | 24 |

A 1.4 kb band was amplified which stained very intensely with ethidium bromide. Other, smaller bands were present, but clearly, the 1.4 kb band was prominent. This band was sequenced and subjected to open reading frame analysis. All of the protein fragments originally sequenced (Table 2), were found in the deduced amino acid sequence of this PCR product.

Southern analysis was performed on genomic DNA using the 1.4 kb cDNA as a radiolabeled probe. Only one band hybridized, suggesting that the gene is a single copy and unique in the *A. phoenices* genome.

Table 1 (pages 4–7) shows the full length cDNA sequence [Seq ID No:1] and deduced amino acid sequence [Seq ID No:2] of the *A. phoenices* oxalate decarboxylase gene as amplified, using PCR primers PHN 12565 and PHN 12567. The underlined amino acid sequences were represented in the original protein sequence analysis data (Table 2). The protein sequence encoded by ihe full length cDNA includes a pre-protein, amino acid residues 27–458 [Seq ID No:4], and a mature protein, amino acid residues 50–458 [Seq ID No:5].

II. These are described in Bidney, et al., 1992, *Plant Mol. Biol.* 18:301–313. The 2×CaMV 35 S promoter is described in Odell, et al., *Nature* 313:810–812.

Figure 3:
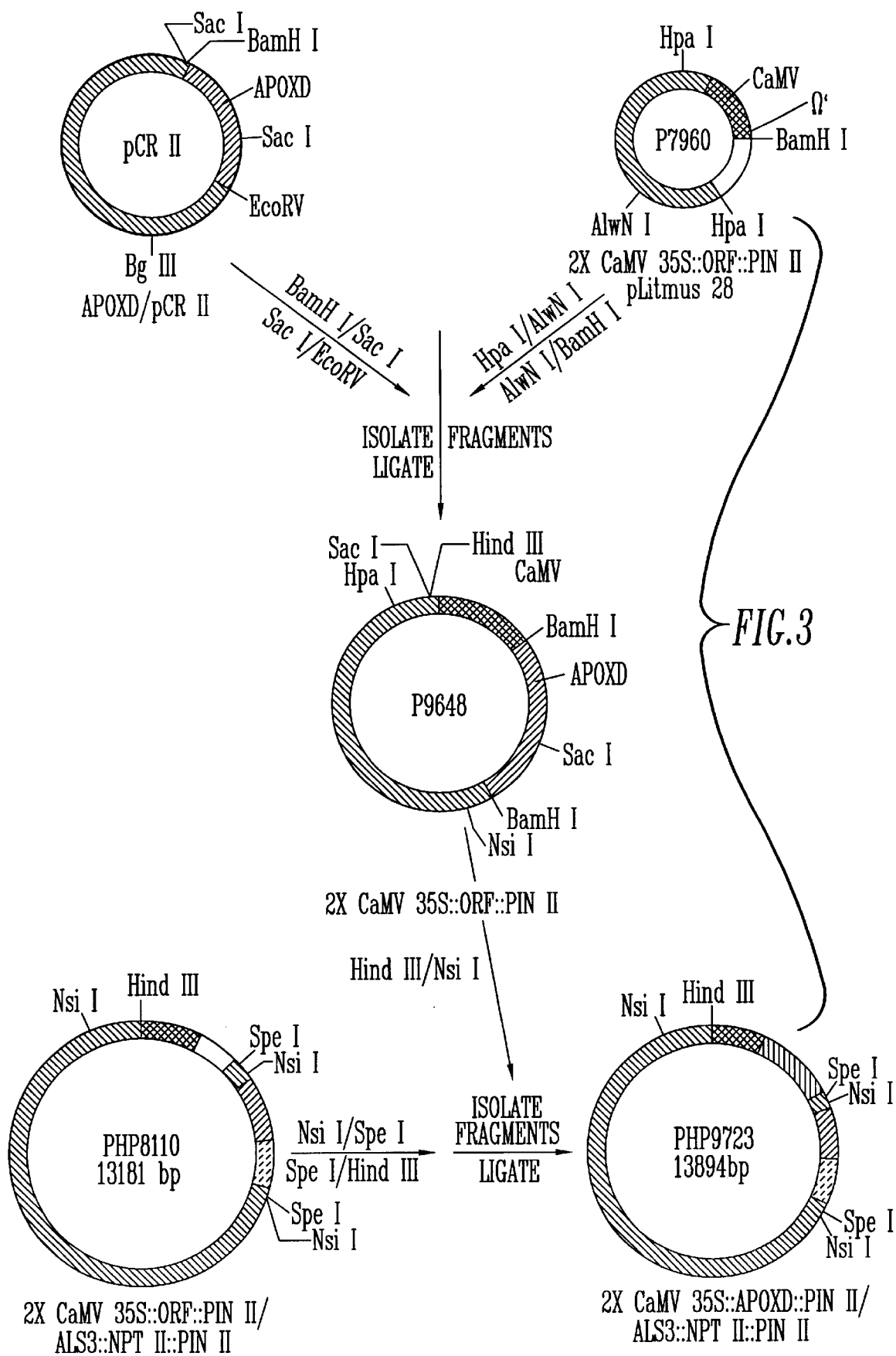
FIG. 3 is a diagram showing the construction of plasmid pPHP9723 containing the 1.4 kb nucleic acid sequence encoding APOXD including leader and pre-sequence.

The plant-expressible APOXD gene cassette was then isolated from the cloning intermediate and ligated into the ALS::NPT II:: PIN II-containing pBIN19 construct, pPHP8110. Plasmid pPHP8110 was created from pBIN 19 (Bevan, 1984, *Nucleic Acids Res.* 12:8711–8721) by replacing the NOS::NPTII::NOS gene cassette in pBIN19 with an ALS::NPTII::PINII cassette. As shown in FIG. 3, pPHP8110 is a derivative of pBIN19 containing the NPT II gene, the aminoglycoside-3'-O-phosphotransferase coding sequence, bases 1551 to 2345 from *E.coli* transposon TN5 (Genbank Accession Number V00004, Beck, et al., 1982, *Gene* 19:327–336). The second amino acid was modified from an isoleucine to a valine in order to create a Nco I restriction site which was used to make a translational fusion with the ALS promoter (see copending U.S. patent application Ser. No. 08/409,297). pPHP8110 further contains the potato proteinase inhibitor II terminator (PIN II) bases 2–310, as described in An, et al., 1989, *Plant Cell* 1:1 15–122.

Figure 4:
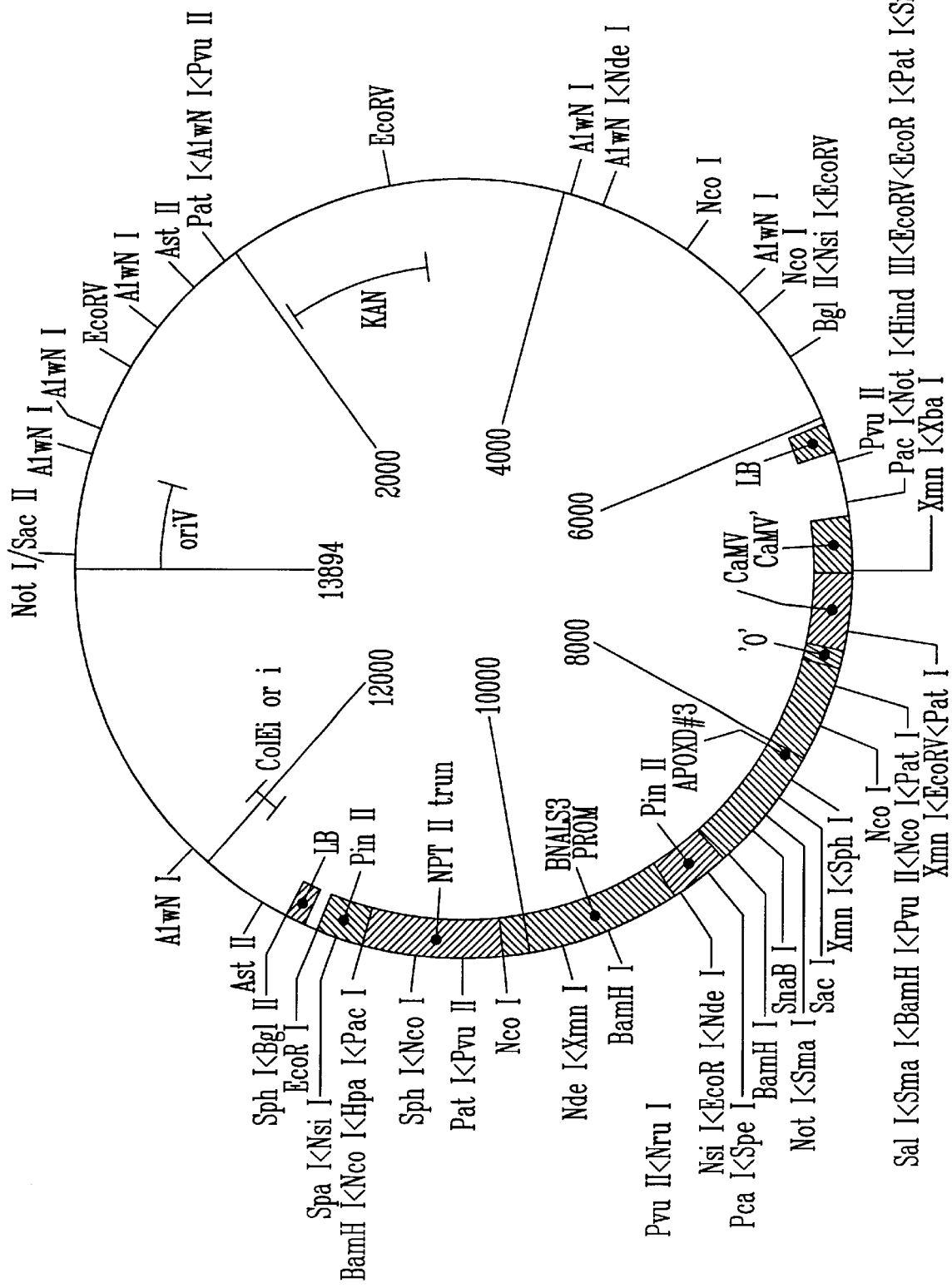
FIG. 4 is a diagram of the plasmid pPHP9723.

As shown in FIG. 4, the resultant plasmid, pPHP9723, carries the APOXD gene construct, together with the NPTII gene for selection of transgenic plant cells, positioned between Agrobacterium T-DNA borders.

Germin/APOXD

A second APOXD cDNA containing plasmid was constructed using the methods described above for producing pPHP 9723. In the second construct, the APOXD fungal signal and presequence (49 amino acids) were replaced with a plant signal sequence obtained from the 5' end of an enzyme subunit of wheat oxalate oxidase. (Lane, et al., 1991, *J. Biol. Chem.* 266:10461.) This was accomplished by designing primers that were homologous to the Germin signal sequence, and having extensions to provide the addition of a Sal I restriction site at the 5' end and APOXD 5' sequence followed by a Nru I site at the 3' end. The primers were used to amplify the Germin signal sequence and are shown below in Table 8.

TABLE 8

| Germin Signal Sequence Primers (5'-3') | Seq ID No. |
|---|---|
| PHN 13418 GAT GAC GCA CAA TCC CAC TAT CCT TCG CAA GAC CCT TC | 25 |
| PHN 13419 GGTT TCG CGATGA TCT GGGG TG AAA GG CTT AT CCT GGG TAG CC AAAA CAG CT GGAG | 26 |

Example 2

Transformed Plant Tissue Degrades Oxalate
CaMV35S/O'/APOXD

The insert of pPHP9685 (1.4 kb APOXD cDNA in pCR II) was placed into a cloning vector intermediate (pLitmus 28, New England Biolabs) between a plant expressible promoter and 3' region as shown in the construction diagrams of FIG. 3. The upstream region consists of a cauliflower mosaic virus 35S promoter with a duplicated enhancer region (2×35S; bases −421 to −90 and −421 to +2, Gardner, et al., 1985, *Nucleic Acids Res.* 9:2871–2888) with a flanking 5' Not1 site and a 3' Pst site, and Ω' RNA leader sequence. The 3' region is from potato proteinase inhibitor The amplified Germin signal sequence product [Seq ID NO:27] shown below in Table 9, and a vector containing the full length APOXD cDNA (pPHP9648) were each digested with Sal I and Nru I. A ligation reaction was set up with the digested fragments to form a Germin signal sequence—APOXD coding sequence fusion construct. Clones of the correct size were sequenced to verify correct results.

As shown in Table 9, the SalI/NruI cut Germin SS—containing sequence also contained modified APOXD codons matched to fill in the NruI-cut APOXD sequence. Germin signal sequence [Seq. ID No: 28] is shown in lower case.

TABLE 9

Amplified Germin Signa/APOXD Sequence*

```
  1 GCAGCTTATT TTTACAACAA TTACCAACAA CAACAAACAA AAACAACAT

SalI                start
 51 TACAATTACT ATTTACAATT ACAGTCGACC CGGGATCC atg ggt tac 98 tca aag acc ttg gtt gct ggt ttg ttc gct atg ttg ttg 137 ttg gct cca gct gtt ttg gct acc |CAG GAT AAG CCT TTC
NruI
176 ACC CCA GAT CAT CGC GACCCCTATG ATCACAAGGT GGATGCGATC

221 GGGGAAGGCC ATGAGCCCTT GCCCTGGCGC ATGGGAGATG GAGCCACCAT

271 CATGGGACCC CGCAACAAGG ACCGTGAGCG CCAGAACCCC GACATGCTCC

311 GTCCTCCGAG CACCGACCAT GGCAACATGC CGAACATGCG GTGGAGCTTT

361 GCTGACTCCC ACATTCGCAT CGAGGAGGGC GGCTGGACAC GCCAGACTAC

411 CGTACGCGAG CTGCCAACGA GCAAGGAGCT TGCGGGTGTA AACATGCGCC

461 TCGATGAGGG TGTCATCCGC GAGTTGCACT GGCATCGA
```

*The SalI (GTCGAC) and NruI (TCGCGA) restriction sites are underlined, the Germin signal sequence is in lower case, with the Germin start site in bold. APOXD sequences modified in the PCR primer design are shown in bold.

This fusion gene was placed in the binary T-DNA plasmid to produce plasmid pPHP9762 carrying the fusion gene and the plant expressible NPTII gene positioned between Agrobacterium T-DNA borders, as described above.

Agrobacterium tumefaciens strain EHA105 (as described in Hood, et al., 1993, Transgen. Res. 2:208–218) was transformed with kanamycin resistant binary T-DNA vectors carrying the different versions of APOXD. Transformation was accomplished by the freeze-thaw method of Holsters, et al., 1978, Mol. Gen. Genetics 1:181–7. The formed isolates were selected on solidified 60A (YEP; 10 g/l yeast extract, 10 g/l bactopeptone, 5 g/l NaCl, pH 7.0) medium with 50 mg/l kanamycin. Transformed bacteria were cultured in liquid culture of YEP medium containing 50 mg/l kanamycin, to log phase growth (O.D.$_{600}$ 0.5–1.0) for use in plant transformations. Binary plasmids were re-isolated from transformed Agrobacterium to verify that integrity was maintained throughout the transformation procedures.

Sunflower leaf discs were obtained by harvesting leaves which were not fully expanded, sterilizing the surface in 20% bleach with TWEEN 20, and punching discs out of the leaf with a paper punch. Agrobacterium suspensions were centrifuged and resuspended in inoculation medium (12.5 $\mu$M MES buffer, pH 5.7, 1 g/l NH$_4$Cl, 0.3 g/l MgSO$_4$) to a calculated OD$_{600}$ of 0.75 as described in Malone-Schoneberg, et al., 1994, Plant Science 103:199–207. Leaf discs were inoculated in the resuspended Agrobacterium for 10 minutes then blotted on sterile filter paper.

The tissue and bacteria were co-cultivated on 527 for 3 days, then transferred to 527E medium for the selection of transgenic plant cells. After 2 weeks of culture, the transgenic callus nodes were removed from the leaf disc and subcultured on fresh 527E medium. A number of subcultures were repeated prior to the assay of the callus tissue for enzyme activity.

To assay for enzyme activity, callus was harvested, snap frozen in liquid nitrogen, lyophilized to dryness and powdered. A quantity of 0.75 mg of powder from each prepared callus line was added to 1.0 ml reaction mixture (900 $\mu$l 200 mM NaPO$_4$, pH 5.0, 100 $\mu$l 10 mM Na-oxalate pH 5.0). The reaction proceeded for 3 hours at room temperature and was stopped by the addition of 150 $\mu$l of 1M TRIS-HCl, pH 7.0. Each sample was spun at 14,000 rpm for one minute and 1 ml was removed to a cuvette. One hundred (100) $\mu$l of 9900-NAD (6.6 mg/ml stock) and 50 $\mu$l formate dehydrogenase (4.0 mg/ml stock) were added and the increase in absorbance was measured at 340 nm. A slope was generated for each sample as well as for a formate standard curve. Assay results were reported as $\mu$M oxalate metabolized/mg powder.

The results of the leaf disk assay are shown below in Table 10, and demonstrate that the APOXD gene sequence produces enzyme that is active in transgenic callus. No activity was seen in control callus, or callus transformed with the native APOXD gene (pPHP 9723).

TABLE 10

Oxalate Decarboxylase Activity in Transgenic Sunflower Tissue

| Callus Line | Binary Vector | Activity $\mu$M oxalate/min/mg |
|---|---|---|
| SMF3 | None | 0 |
| 9723 -1 | pPHP 9723 | 0 |
| -2 | pPHP 9723 | 0 |
| -3 | pPHP 9723 | 0 |
| 9762 -1 | pPHP 9762 | 1.35 |
| -2 | pPHP 9762 | 1.40 |
| -3 | pPHP 9762 | 0.87 |
| -4 | pPHP 9762 | 0.81 |
| -5 | pPHP 9762 | 0.81 |
| -6 | pPHP 9762 | 0.90 |

Example 3

Transgenic Sunflower Plants Expressing APOXD

Sunflower plants were transformed using a basic transformation protocol involving a combination of wounding by particle bombardment, followed by use of Agrobacterium for DNA delivery, as described by Bidney, et al. *Plant Mol. Biol.* 18:301–313. The plasmid pPHP9762, as described above for Example 2 and shown in FIG. 5, was used in these experiments. pPHP9762 contains the APOXD gene with the fungal signal and presequence replaced with the Germin signal sequence and a plant expressible NPTII gene which provides kanamycin resistance to transgenic plant tissues.

Procedures for preparation of Agrobacterium and preparation of particles for wounding are described in Bidney, et al., 1992, *Plant Mol. Biol.* 18:301–313. The Pioneer sunflower line SMF3, used in these experiments, is described in Burrus, et al., 1991, *Plant Cell Rep.* 10:161–166. The Agrobacterium strain used in these experiments, EHA 105. Procedures for use of the helium gun, intact meristem preparation, tissue culture and co-cultivation conditions, as well as recovery of transgenic plants, are described in Bidney, et al., 1992, *Plant Mol. Biol.* 18:301–13.

Sunflower explants were prepared by imbibing seed overnight, removing the cotyledons and radical tip, then culturing overnight on medium containing plant growth regulators. Primary leaves were then removed and explants arranged in the center of a petri plate for bombardment. The PDS 1000 helium-driven particle bombardment device (Bio-Rad) was used with 600 psi rupture discs and a vacuum of 26 inches, Hg to bombard meristem explants twice on the highest shelf position. Following bombardment, log phase Agrobacterium cultures transformed with the APOXD-plasmid pPHP 9762, as described for Example 2, were centrifuged and resuspended at a calculated OD600 (vis) of 4.0 in inoculation buffer. Agrobacterium was then dropped onto the meristem explants using a fine tipped pipettor. Inoculated explants were co-cultured for three days then transferred to medium containing 50 mg/l kanamycin and 250 mg/l cefotaxime for selection. Explants were cultured on this medium for two weeks then transferred to the same medium, but lacking kanamycin. Green, kanamycin-resistant shoots were recovered to the greenhouse and assayed by an NPTII ELISA assay to verify transformation. Oxalate decarboxylase enzyme assays are performed on these plants and/or progeny to confirm the expression of APOXD.

The invention has been described with reference to various specific and preferred embodiments and techniques. However, it should be understood that many variations and modifications may be made while remaining within the spirit and scope of the invention.

We claim:

1. A method of increasing resistance in a plant to Sclerotinia or Sclerotium, the method comprising:
   a) transforming a plant or plant cell with a nucleic acid encoding an oxalate decarboxylase having the amino acid sequence set forth in SEQ ID NO: 2 or SEQ ID NO: 5;
   b) culturing the plant cell under plant growing conditions to produce a regenerated plant; and
   c) inducing expression of said polypeptide for a time sufficient to increase resistance to Sclerotinia or Sclerotium.

2. The method of claim 1 wherein the plant or plant cell is selected from the group consisting of sunflower, bean, canola, alfalfa, soybean, flax, safflower, peanut and clover.

3. The method of claim 1 wherein the nucleic acid is shown in SEQ ID NO: 1.

4. The method of claim 1 wherein the plant or plant cell is selected from the group consisting of sunflower, bean, canola, alfalfa, soybean, flax, safflower, peanut and clover.

5. A method of increasing resistance in a plant to Sclerotinia or Sclerotium, the method comprising:
   a) transforming a plant or plant cell with a nucleic acid having the sequence of the *Aspergillus phoenices* oxalate decarboxylase insert in the plasmid ATCC No. 97959;
   b) culturing the plant cell under plant growing conditions to produce a regenerated plant; and
   c) inducing expression of said oxalate decarboxylase for a time sufficient to increase resistance to Sclerotinia or Sclerotium.

* * * * *

SEQUENCE LISTING

```
<160> NUMBER OF SEQ ID NOS: 30

<210> SEQ ID NO 1
<211> LENGTH: 1438
<212> TYPE: DNA
<213> ORGANISM: Aspergillus phoenices
<220> FEATURE:
<221> NAME/KEY: CDS
<222> LOCATION: (24)...(1394)
<221> NAME/KEY: mat_peptide
<222> LOCATION: (171)...(1394)
<221> NAME/KEY: sig_peptide
<222> LOCATION: (24)...(101)

<400> SEQUENCE: 1
ggcttgtcag gatccttcca aag atg cag cta acc ctg cca cca cgt cag ctg      53
                         Met Gln Leu Thr Leu Pro Pro Arg Gln Leu
                          1               5                  10 ttg ctg agt ttc gcg acc gtg gcc gcc ctc ctt gat cca agc cat gga       101
Leu Leu Ser Phe Ala Thr Val Ala Ala Leu Leu Asp Pro Ser His Gly
                 15                  20                  25 ggc ccg gtc cct aac gaa gcg tac cag caa cta ctg cag att ccc gcc       149
Gly Pro Val Pro Asn Glu Ala Tyr Gln Gln Leu Leu Gln Ile Pro Ala
             30                  35                  40 tca tcc cca tcc att ttc ttc caa gac aag cca ttc acc ccc gat cat       197
Ser Ser Pro Ser Ile Phe Phe Gln Asp Lys Pro Phe Thr Pro Asp His
         45                  50                  55 cgc gac ccc tat gat cac aag gtg gat gcg atc ggg gaa ggc cat gag       245
Arg Asp Pro Tyr Asp His Lys Val Asp Ala Ile Gly Glu Gly His Glu
     60                  65                  70 ccc ttg ccc tgg cgc atg gga gat gga gcc acc atc atg gga ccc cgc       293
Pro Leu Pro Trp Arg Met Gly Asp Gly Ala Thr Ile Met Gly Pro Arg
 75                  80                  85                  90 aac aag gac cgt gag cgc cag aac ccc gac atg ctc cgt cct ccg agc       341
Asn Lys Asp Arg Glu Arg Gln Asn Pro Asp Met Leu Arg Pro Pro Ser
                 95                 100                 105 acc gac cat ggc aac atg ccg aac atg cgg tgg agc ttt gct gac tcc       389
```

```
Thr Asp His Gly Asn Met Pro Asn Met Arg Trp Ser Phe Ala Asp Ser
        110                 115                 120 cac att cgc atc gag gag ggc ggc tgg aca cgc cag act acc gta cgc              437
His Ile Arg Ile Glu Glu Gly Gly Trp Thr Arg Gln Thr Thr Val Arg
        125                 130                 135 gag ctg cca acg agc aag gag ctt gcg ggt gta aac atg cgc ctc gat              485
Glu Leu Pro Thr Ser Lys Glu Leu Ala Gly Val Asn Met Arg Leu Asp
        140                 145                 150 gag ggt gtc atc cgc gag ttg cac tgg cat cga gaa gca gag tgg gcg              533
Glu Gly Val Ile Arg Glu Leu His Trp His Arg Glu Ala Glu Trp Ala
155                 160                 165                 170 tat gtg ctg gcc gga cgt gta cga gtg act ggc ctt gac ctg gag gga              581
Tyr Val Leu Ala Gly Arg Val Arg Val Thr Gly Leu Asp Leu Glu Gly
                175                 180                 185 ggc agc ttc atc gac gac cta gaa gag ggt gac ctc tgg tac ttc cca              629
Gly Ser Phe Ile Asp Asp Leu Glu Glu Gly Asp Leu Trp Tyr Phe Pro
                190                 195                 200 tcg ggc cat ccc cat tcg ctt cag ggt ctc agt cct aat ggc acc gag              677
Ser Gly His Pro His Ser Leu Gln Gly Leu Ser Pro Asn Gly Thr Glu
                205                 210                 215 ttc tta ctg atc ttc gac gat gga aac ttt tcc gag gag tca acg ttc              725
Phe Leu Leu Ile Phe Asp Asp Gly Asn Phe Ser Glu Glu Ser Thr Phe
        220                 225                 230 ttg ttg acc gac tgg atc gca cat aca ccc aag tct gtc ctc gcc gga              773
Leu Leu Thr Asp Trp Ile Ala His Thr Pro Lys Ser Val Leu Ala Gly
235                 240                 245                 250 aac ttc cgc atg cgc cca caa aca ttt aag aac atc cca cca tct gaa              821
Asn Phe Arg Met Arg Pro Gln Thr Phe Lys Asn Ile Pro Pro Ser Glu
                255                 260                 265 aag tac atc ttc cag ggc tct gtc cca gac tct att ccc aaa gag ctc              869
Lys Tyr Ile Phe Gln Gly Ser Val Pro Asp Ser Ile Pro Lys Glu Leu
                270                 275                 280 ccc cgc aac ttc aaa gca tcc aag cag cgc ttc acg cat aag atg ctc              917
Pro Arg Asn Phe Lys Ala Ser Lys Gln Arg Phe Thr His Lys Met Leu
        285                 290                 295 gct caa aaa ccc gaa cat acc tct ggc gga gag gtg cgc atc aca gac              965
Ala Gln Lys Pro Glu His Thr Ser Gly Gly Glu Val Arg Ile Thr Asp
        300                 305                 310 tcg tcc aac ttt ccc atc tcc aag acg gtc gcg gcc gcc cac ctg acc             1013
Ser Ser Asn Phe Pro Ile Ser Lys Thr Val Ala Ala Ala His Leu Thr
315                 320                 325                 330 att aac ccg ggt gct atc cgg gag atg cac tgg cat ccc aat gcg gat             1061
Ile Asn Pro Gly Ala Ile Arg Glu Met His Trp His Pro Asn Ala Asp
                335                 340                 345 gaa tgg tcc tac ttt aag cgc ggt cgg gcg cga gtg act atc ttc gct             1109
Glu Trp Ser Tyr Phe Lys Arg Gly Arg Ala Arg Val Thr Ile Phe Ala
                350                 355                 360 gct gaa ggt aat gct cgt acg ttc gac tac gta gcg gga gat gtg ggc             1157
Ala Glu Gly Asn Ala Arg Thr Phe Asp Tyr Val Ala Gly Asp Val Gly
                365                 370                 375 att gtt cct cgc aac atg ggt cat ttc att gag aac ctt agt gat gac             1205
Ile Val Pro Arg Asn Met Gly His Phe Ile Glu Asn Leu Ser Asp Asp
        380                 385                 390 gag gag gtc gag gtg ttg gaa atc ttc cgg gcg gac cga ttc cgg gac             1253
Glu Glu Val Glu Val Leu Glu Ile Phe Arg Ala Asp Arg Phe Arg Asp
395                 400                 405                 410 ttt tct ttg ttc cag tgg atg gga gag acg ccg cag cgg atg gtg gca             1301
Phe Ser Leu Phe Gln Trp Met Gly Glu Thr Pro Gln Arg Met Val Ala
                415                 420                 425
```

-continued

| | | | | | | | | | | | | |
|---|---|---|---|---|---|---|---|---|---|---|---|---|
| gag | cat | gtg | ttt | aag | gat | gat | cca | gat | gcg | gcc | agg | gag | ttc | ctt | aag | 1349 |
| Glu | His | Val | Phe | Lys | Asp | Asp | Pro | Asp | Ala | Ala | Arg | Glu | Phe | Leu | Lys | |
| | | | 430 | | | | 435 | | | | 440 | | | | | |

| | | | | | | | | | | | |
|---|---|---|---|---|---|---|---|---|---|---|---|
| agt | gtg | gag | agt | ggg | gag | aag | gat | cca | att | cgg | agc | cca | agt | gag | 1394 |
| Ser | Val | Glu | Ser | Gly | Glu | Lys | Asp | Pro | Ile | Arg | Ser | Pro | Ser | Glu | |
| | | | 445 | | | | 450 | | | | 455 | | | | | tagatgaggt tctacgcgtg tattttgctg atatcatcga agcc     1438

<210> SEQ ID NO 2
<211> LENGTH: 457
<212> TYPE: PRT
<213> ORGANISM: Aspergillus phoenices

<400> SEQUENCE: 2

Met Gln Leu Thr Leu Pro Pro Arg Gln Leu Leu Ser Phe Ala Thr
1               5                  10                 15

Val Ala Ala Leu Leu Asp Pro Ser His Gly Gly Pro Val Pro Asn Glu
            20                 25                 30

Ala Tyr Gln Gln Leu Leu Gln Ile Pro Ala Ser Ser Pro Ser Ile Phe
        35                 40                 45

Phe Gln Asp Lys Pro Phe Thr Pro Asp His Arg Asp Pro Tyr Asp His
    50                 55                 60

Lys Val Asp Ala Ile Gly Glu Gly His Glu Pro Leu Pro Trp Arg Met
65                 70                 75                 80

Gly Asp Gly Ala Thr Ile Met Gly Pro Arg Asn Lys Asp Arg Glu Arg
                85                 90                 95

Gln Asn Pro Asp Met Leu Arg Pro Pro Ser Thr Asp His Gly Asn Met
            100                105                110

Pro Asn Met Arg Trp Ser Phe Ala Asp Ser His Ile Arg Ile Glu Glu
        115                120                125

Gly Gly Trp Thr Arg Gln Thr Thr Val Arg Glu Leu Pro Thr Ser Lys
    130                135                140

Glu Leu Ala Gly Val Asn Met Arg Leu Asp Glu Gly Val Ile Arg Glu
145                150                155                160

Leu His Trp His Arg Glu Ala Glu Trp Ala Tyr Val Leu Ala Gly Arg
                165                170                175

Val Arg Val Thr Gly Leu Asp Leu Glu Gly Gly Ser Phe Ile Asp Asp
            180                185                190

Leu Glu Glu Gly Asp Leu Trp Tyr Phe Pro Ser Gly His Pro His Ser
        195                200                205

Leu Gln Gly Leu Ser Pro Asn Gly Thr Glu Phe Leu Leu Ile Phe Asp
    210                215                220

Asp Gly Asn Phe Ser Glu Glu Ser Thr Phe Leu Leu Thr Asp Trp Ile
225                230                235                240

Ala His Thr Pro Lys Ser Val Leu Ala Gly Asn Phe Arg Met Arg Pro
                245                250                255

Gln Thr Phe Lys Asn Ile Pro Pro Ser Glu Lys Tyr Ile Phe Gln Gly
            260                265                270

Ser Val Pro Asp Ser Ile Pro Lys Glu Leu Pro Arg Asn Phe Lys Ala
        275                280                285

Ser Lys Gln Arg Phe Thr His Lys Met Leu Ala Gln Lys Pro Glu His
    290                295                300

Thr Ser Gly Gly Glu Val Arg Ile Thr Asp Ser Ser Asn Phe Pro Ile
305                310                315                320

Ser Lys Thr Val Ala Ala Ala His Leu Thr Ile Asn Pro Gly Ala Ile

```
                       325                 330                 335
Arg Glu Met His Trp His Pro Asn Ala Asp Glu Trp Ser Tyr Phe Lys
            340                 345                 350

Arg Gly Arg Ala Arg Val Thr Ile Phe Ala Ala Glu Gly Asn Ala Arg
            355                 360                 365

Thr Phe Asp Tyr Val Ala Gly Asp Val Gly Ile Val Pro Arg Asn Met
            370                 375                 380

Gly His Phe Ile Glu Asn Leu Ser Asp Asp Glu Val Glu Val Leu
385                 390                 395                 400

Glu Ile Phe Arg Ala Asp Arg Phe Arg Asp Phe Ser Leu Phe Gln Trp
                    405                 410                 415

Met Gly Glu Thr Pro Gln Arg Met Val Ala Glu His Val Phe Lys Asp
            420                 425                 430

Asp Pro Asp Ala Ala Arg Glu Phe Leu Lys Ser Val Glu Ser Gly Glu
            435                 440                 445

Lys Asp Pro Ile Arg Ser Pro Ser Glu
450                 455

<210> SEQ ID NO 3
<211> LENGTH: 26
<212> TYPE: PRT
<213> ORGANISM: Aspergillus phoenices

<400> SEQUENCE: 3

Met Gln Leu Thr Leu Pro Pro Arg Gln Leu Leu Leu Ser Phe Ala Thr
1               5                   10                  15

Val Ala Ala Leu Leu Asp Pro Ser His Gly
            20                  25

<210> SEQ ID NO 4
<211> LENGTH: 431
<212> TYPE: PRT
<213> ORGANISM: Aspergillus phoenices

<400> SEQUENCE: 4

Gly Pro Val Pro Asn Glu Ala Tyr Gln Gln Leu Leu Gln Ile Pro Ala
1               5                   10                  15

Ser Ser Pro Ser Ile Phe Phe Gln Asp Lys Pro Phe Thr Pro Asp His
            20                  25                  30

Arg Asp Pro Tyr Asp His Lys Val Asp Ala Ile Gly Glu Gly His Glu
            35                  40                  45

Pro Leu Pro Trp Arg Met Gly Asp Gly Ala Thr Ile Met Gly Pro Arg
            50                  55                  60

Asn Lys Asp Arg Glu Arg Gln Asn Pro Asp Met Leu Arg Pro Pro Ser
65                  70                  75                  80

Thr Asp His Gly Asn Met Pro Asn Met Arg Trp Ser Phe Ala Asp Ser
            85                  90                  95

His Ile Arg Ile Glu Glu Gly Gly Trp Thr Arg Gln Thr Thr Val Arg
            100                 105                 110

Glu Leu Pro Thr Ser Lys Glu Leu Ala Gly Val Asn Met Arg Leu Asp
            115                 120                 125

Glu Gly Val Ile Arg Glu Leu His Trp His Arg Glu Ala Glu Trp Ala
            130                 135                 140

Tyr Val Leu Ala Gly Arg Val Arg Val Thr Gly Leu Asp Leu Glu Gly
145                 150                 155                 160

Gly Ser Phe Ile Asp Asp Leu Glu Glu Gly Asp Leu Trp Tyr Phe Pro
```

```
                        165                 170                 175
    Ser Gly His Pro His Ser Leu Gln Gly Leu Ser Pro Asn Gly Thr Glu
                    180                 185                 190

Phe Leu Leu Ile Phe Asp Asp Gly Asn Phe Ser Glu Glu Ser Thr Phe
                195                 200                 205

Leu Leu Thr Asp Trp Ile Ala His Thr Pro Lys Ser Val Leu Ala Gly
            210                 215                 220

Asn Phe Arg Met Arg Pro Gln Thr Phe Lys Asn Ile Pro Pro Ser Glu
    225                 230                 235                 240

Lys Tyr Ile Phe Gln Gly Ser Val Pro Asp Ser Ile Pro Lys Glu Leu
                    245                 250                 255

Pro Arg Asn Phe Lys Ala Ser Lys Gln Arg Phe Thr His Lys Met Leu
                260                 265                 270

Ala Gln Lys Pro Glu His Thr Ser Gly Gly Glu Val Arg Ile Thr Asp
                275                 280                 285

Ser Ser Asn Phe Pro Ile Ser Lys Thr Val Ala Ala His Leu Thr
            290                 295                 300

Ile Asn Pro Gly Ala Ile Arg Glu Met His Trp His Pro Asn Ala Asp
    305                 310                 315                 320

Glu Trp Ser Tyr Phe Lys Arg Gly Arg Ala Arg Val Thr Ile Phe Ala
                    325                 330                 335

Ala Glu Gly Asn Ala Arg Thr Phe Asp Tyr Val Ala Gly Asp Val Gly
                340                 345                 350

Ile Val Pro Arg Asn Met Gly His Phe Ile Glu Asn Leu Ser Asp Asp
            355                 360                 365

Glu Glu Val Glu Val Leu Glu Ile Phe Arg Ala Asp Arg Phe Arg Asp
        370                 375                 380

Phe Ser Leu Phe Gln Trp Met Gly Glu Thr Pro Gln Arg Met Val Ala
    385                 390                 395                 400

Glu His Val Phe Lys Asp Asp Pro Asp Ala Ala Arg Glu Phe Leu Lys
                    405                 410                 415

Ser Val Glu Ser Gly Glu Lys Asp Pro Ile Arg Ser Pro Ser Glu
                420                 425                 430

<210> SEQ ID NO 5
<211> LENGTH: 408
<212> TYPE: PRT
<213> ORGANISM: Aspergillus phoenices

<400> SEQUENCE: 5

Gln Asp Lys Pro Phe Thr Pro Asp His Arg Asp Pro Tyr Asp His Lys
    1               5                   10                  15

Val Asp Ala Ile Gly Glu Gly His Glu Pro Leu Pro Trp Arg Met Gly
                    20                  25                  30

Asp Gly Ala Thr Ile Met Gly Pro Arg Asn Lys Asp Arg Glu Arg Gln
                35                  40                  45

Asn Pro Asp Met Leu Arg Pro Pro Ser Thr Asp His Gly Asn Met Pro
            50                  55                  60

Asn Met Arg Trp Ser Phe Ala Asp Ser His Ile Arg Ile Glu Glu Gly
    65                  70                  75                  80

Gly Trp Thr Arg Gln Thr Thr Val Arg Glu Leu Pro Thr Ser Lys Glu
                    85                  90                  95

Leu Ala Gly Val Asn Met Arg Leu Asp Glu Gly Val Ile Arg Glu Leu
                100                 105                 110
```

```
His Trp His Arg Glu Ala Glu Trp Ala Tyr Val Leu Ala Gly Arg Val
        115                 120                 125

Arg Val Thr Gly Leu Asp Leu Glu Gly Gly Ser Phe Ile Asp Asp Leu
130                 135                 140

Glu Glu Gly Asp Leu Trp Tyr Phe Pro Ser Gly His Pro His Ser Leu
145                 150                 155                 160

Gln Gly Leu Ser Pro Asn Gly Thr Glu Phe Leu Leu Ile Phe Asp Asp
                165                 170                 175

Gly Asn Phe Ser Glu Glu Ser Thr Phe Leu Leu Thr Asp Trp Ile Ala
            180                 185                 190

His Thr Pro Lys Ser Val Leu Ala Gly Asn Phe Arg Met Arg Pro Gln
        195                 200                 205

Thr Phe Lys Asn Ile Pro Pro Ser Glu Lys Tyr Ile Phe Gln Gly Ser
    210                 215                 220

Val Pro Asp Ser Ile Pro Lys Glu Leu Pro Arg Asn Phe Lys Ala Ser
225                 230                 235                 240

Lys Gln Arg Phe Thr His Lys Met Leu Ala Gln Lys Pro Glu His Thr
                245                 250                 255

Ser Gly Gly Glu Val Arg Ile Thr Asp Ser Ser Asn Phe Pro Ile Ser
            260                 265                 270

Lys Thr Val Ala Ala His Leu Thr Ile Asn Pro Gly Ala Ile Arg
        275                 280                 285

Glu Met His Trp His Pro Asn Ala Asp Glu Trp Ser Tyr Phe Lys Arg
        290                 295                 300

Gly Arg Ala Arg Val Thr Ile Phe Ala Ala Glu Gly Asn Ala Arg Thr
305                 310                 315                 320

Phe Asp Tyr Val Ala Gly Asp Val Gly Ile Val Pro Arg Asn Met Gly
                325                 330                 335

His Phe Ile Glu Asn Leu Ser Asp Asp Glu Glu Val Glu Val Leu Glu
            340                 345                 350

Ile Phe Arg Ala Asp Arg Phe Arg Asp Phe Ser Leu Phe Gln Trp Met
        355                 360                 365

Gly Glu Thr Pro Gln Arg Met Val Ala Glu His Val Phe Lys Asp Asp
    370                 375                 380

Pro Asp Ala Ala Arg Glu Phe Leu Lys Ser Val Glu Ser Gly Lys
385                 390                 395                 400

Asp Pro Ile Arg Ser Pro Ser Glu
                405

<210> SEQ ID NO 6
<211> LENGTH: 27
<212> TYPE: PRT
<213> ORGANISM: Aspergillus phoenices
<220> FEATURE:
<221> NAME/KEY: VARIANT
<222> LOCATION: (1)...(27)
<223> OTHER INFORMATION: Xaa = Any Amino Acid

<400> SEQUENCE: 6

Gln Asp Lys Pro Phe Thr Pro Asp His Arg Asp Pro Tyr Asp His Lys
1               5                   10                  15

Val Asp Ala Ile Gly Glu Xaa His Glu Pro Leu
            20                  25

<210> SEQ ID NO 7
<211> LENGTH: 12
<212> TYPE: PRT
```

```
<213> ORGANISM: Aspergillus phoenices

<400> SEQUENCE: 7

Val Ile Arg Glu Leu His Trp His Arg Glu Ala Gly
  1               5                  10

<210> SEQ ID NO 8
<211> LENGTH: 17
<212> TYPE: PRT
<213> ORGANISM: Aspergillus phoenices

<400> SEQUENCE: 8

Arg Leu Asp Glu Gly Val Ile Arg Glu Leu His Cys His Arg Glu Ala
  1               5                  10                  15

Glu

<210> SEQ ID NO 9
<211> LENGTH: 20
<212> TYPE: PRT
<213> ORGANISM: Aspergillus phoenices

<400> SEQUENCE: 9

Ser Tyr Phe Lys Arg Gly Arg Ala Arg Tyr Thr Ile Phe Ala Ala Glu
  1               5                  10                  15

Gly Asn Ala Arg
            20

<210> SEQ ID NO 10
<211> LENGTH: 12
<212> TYPE: PRT
<213> ORGANISM: Aspergillus phoenices

<400> SEQUENCE: 10

Ser Ala His Thr Pro Pro Ser Val Leu Ala Gly Asn
  1               5                  10

<210> SEQ ID NO 11
<211> LENGTH: 35
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(35)
<223> OTHER INFORMATION: n = A,T,C or G

<400> SEQUENCE: 11
caucaucauc auccatggga ycaycgngay ccyta                         35

<210> SEQ ID NO 12
<211> LENGTH: 35
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(35)
<223> OTHER INFORMATION: n = A,T,C or G

<400> SEQUENCE: 12
cuacuacuac uaaggcctgt gnrrytcncg datva                         35

<210> SEQ ID NO 13
<211> LENGTH: 22
<212> TYPE: DNA
```

```
<213> ORGANISM: Artificial Sequence
<220> FEATURE:
<223> OTHER INFORMATION: primer

<400> SEQUENCE: 13
caccatggta cgatcacaag gt                                             22

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
tcaacgtgac cgttccggac t                                              21

<210> SEQ ID NO 15
<211> LENGTH: 440
<212> TYPE: DNA
<213> ORGANISM: Aspergillus phoenices
<220> FEATURE:
<221> NAME/KEY: CDS
<222> LOCATION: (3)...(197)
<221> NAME/KEY: CDS
<222> LOCATION: (259)...(360)

<400> SEQUENCE: 15 ac gat cac aag gtg gat gcg atc ggg gaa ggc cat gag ccc ttg ccc       47
   Asp His Lys Val Asp Ala Ile Gly Glu Gly His Glu Pro Leu Pro
    1               5                  10                  15 tgg cgc atg gga gat gga gcc acc atc atg gga ccc cgc aac aag gac      95
Trp Arg Met Gly Asp Gly Ala Thr Ile Met Gly Pro Arg Asn Lys Asp
            20                  25                  30 cgt gag cgc cag aac ccc gac atg ctc cgt cct ccg agc acc gac cat     143
Arg Glu Arg Gln Asn Pro Asp Met Leu Arg Pro Pro Ser Thr Asp His
        35                  40                  45 ggc aac atg ccg aac atg cgg tgg agc ttt gct gac tcc cac att cgc     191
Gly Asn Met Pro Asn Met Arg Trp Ser Phe Ala Asp Ser His Ile Arg
    50                  55                  60 atc gag gtaagcccctt cgagggtttt gtgtacgaca agcaaaatag gctaatgcac    247
Ile Glu
    65 tgcaggaggg c ggc tgg aca cgc cag act acc gta cgc gag ctg cca acg     297
             Gly Trp Thr Arg Gln Thr Thr Val Arg Glu Leu Pro Thr
                              70                  75 agc aag gag ctt gcg ggt gta aac atg cgc ctc gat gag ggt gtc atc     345
Ser Lys Glu Leu Ala Gly Val Asn Met Arg Leu Asp Glu Gly Val Ile
    80                  85                  90 cgc gag ttg cac tgg caagggctga aggcgaattc cagcacactg gcggccgtta    400
Arg Glu Leu His Trp
 95 ctagtggatc cgagctcggt accaagcttg atgcatagct                         440

<210> SEQ ID NO 16
<211> LENGTH: 99
<212> TYPE: PRT
<213> ORGANISM: Aspergillus phoenices

<400> SEQUENCE: 16

Asp His Lys Val Asp Ala Ile Gly Glu Gly His Glu Pro Leu Pro Trp
 1               5                  10                  15

Arg Met Gly Asp Gly Ala Thr Ile Met Gly Pro Arg Asn Lys Asp Arg
            20                  25                  30
```

```
Glu Arg Gln Asn Pro Asp Met Leu Arg Pro Ser Thr Asp His Gly
         35                  40                  45

Asn Met Pro Asn Met Arg Trp Ser Phe Ala Asp Ser His Ile Arg Ile
 50                  55                  60

Glu Gly Trp Thr Arg Gln Thr Thr Val Arg Glu Leu Pro Thr Ser Lys
 65                  70                  75                  80

Glu Leu Ala Gly Val Asn Met Arg Leu Asp Glu Gly Val Ile Arg Glu
                     85                  90                  95

Leu His Trp
```

```
<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
aacatgcggt ggagctttg                                           19

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
caucaucauc aucattcgca tcgaggtaag                                30

<210> SEQ ID NO 19
<211> LENGTH: 28
<212> TYPE: DNA
<213> ORGANISM: Artificial Sequence
<220> FEATURE:
<223> OTHER INFORMATION: primer

<400> SEQUENCE: 19
cgcggatccg tttttttttt tttttttv                                 28

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
taaggatcct gggggggggg gggh                                     24

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
caucaucauc autacctcga tgcgaatgtg                                30

<210> SEQ ID NO 22
<211> LENGTH: 28
<212> TYPE: DNA
```

```
<213> ORGANISM: Artificial Sequence
<220> FEATURE:
<223> OTHER INFORMATION: primer

<400> SEQUENCE: 22
cgatgatatc agcaaaatac acgcgtag                                        28

<210> SEQ ID NO 23
<211> LENGTH: 26
<212> TYPE: DNA
<213> ORGANISM: Artificial Sequence
<220> FEATURE:
<223> OTHER INFORMATION: primer

<400> SEQUENCE: 23
gtcaggatcc cgcttcatcc ccatcc                                          26

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
catgatatcc tactcacttg ggctccg                                         27

<210> SEQ ID NO 25
<211> LENGTH: 38
<212> TYPE: DNA
<213> ORGANISM: Artificial Sequence
<220> FEATURE:
<223> OTHER INFORMATION: primer

<400> SEQUENCE: 25
gatgacgcac aatcccacta tccttcgcaa gacccttc                             38

<210> SEQ ID NO 26
<211> LENGTH: 56
<212> TYPE: DNA
<213> ORGANISM: Artificial Sequence
<220> FEATURE:
<223> OTHER INFORMATION: primer

<400> SEQUENCE: 26
ggtttcgcga tgatctgggg tgaaaggctt atcctgggta gccaaaacag ctggag         56

<210> SEQ ID NO 27
<211> LENGTH: 507
<212> TYPE: DNA
<213> ORGANISM: Triticum aestivum

<400> SEQUENCE: 27
gcagcttatt tttacaacaa ttaccaacaa caacaaacaa aaacaacatt acaattacta     60
tttacaatta cagtcgaccc gggatccatg ggttactcaa agaccttggt tgctggtttg    120
ttcgctatgt tgttgttggc tccagctgtt ttggctaccc aggataagcc tttcaccca     180 gatcatcgcg acccctatga tcacaaggtg gatgcgatcg gggaaggcca tgagcccttg    240
ccctggcgca tgggagatgg agccaccatc atgggacccc gcaacaagga ccgtgagcgc    300
cagaaccccg acatgctccg tcctccgagc accgaccatg gcaacatgcc gaacatgcgg    360
tggagctttg ctgactccac cattcgcatc gaggagggcg gctggacacg ccagactacc    420
gtacgcgagc tgccaacgag caaggagctt gcgggtgtaa acatgcgcct cgatgagggt    480
```

-continued

```
gtcatccgcg agttgcactg gcatcga                                        507

<210> SEQ ID NO 28
<211> LENGTH: 72
<212> TYPE: DNA
<213> ORGANISM: Triticum aestivum

<400> SEQUENCE: 28
atgggttact caaagacctt ggttgctggt ttgttcgcta tgttgttgtt ggctccagct    60
gttttggcta cc                                                        72

<210> SEQ ID NO 29
<211> LENGTH: 16
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(16)
<223> OTHER INFORMATION: n = A,T,C or G

<400> SEQUENCE: 29
nggggggggg gggatc                                                    16

<210> SEQ ID NO 30
<211> LENGTH: 17
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(17)
<223> OTHER INFORMATION: n = A,T,C or G

<400> SEQUENCE: 30 ntttttttttt ttttttt                                                  17
```